United States Patent [19]

Turner et al.

[11] Patent Number: 5,384,299

[45] Date of Patent: * Jan. 24, 1995

[54] IONIC METALLOCENE CATALYST COMPOSITIONS

[75] Inventors: Howard W. Turner; Gregory G. Hlatky; Richard R. Eckman, all of Houston, Tex.

[73] Assignee: Exxon Chemical Patents Inc., Linden, N.J.

[*] Notice: The portion of the term of this patent subsequent to Mar. 30, 2010 has been disclaimed.

[21] Appl. No.: 19,726

[22] Filed: Feb. 19, 1993

Related U.S. Application Data

[63] Continuation-in-part of Ser. No. 737,611, Jul. 30, 1991, Pat. No. 5,198,401, which is a continuation-in-part of Ser. No. 555,977, Jun. 19, 1990, abandoned, which is a continuation-in-part of Ser. No. 133,480, Dec. 22, 1987, abandoned, which is a continuation-in-part of Ser. No. 8,800, Jan. 30, 1987, abandoned, which is a continuation-in-part of Ser. No. 133,052, Dec. 22, 1987, abandoned, which is a continuation-in-part of Ser. No. 11,471, Jan. 30, 1987, abandoned.

[51] Int. Cl.$^6$ .............................. C08F 4/643
[52] U.S. Cl. ...................... 502/155; 502/103; 502/104; 502/117; 502/152
[58] Field of Search ............... 502/103, 104, 117, 152, 502/155

[56] References Cited

U.S. PATENT DOCUMENTS

| | | | |
|---|---|---|---|
| 5,064,802 | 11/1991 | Stevens et al. | 502/155 |
| 5,155,080 | 10/1992 | Elder et al. | 502/152 |
| 5,162,278 | 11/1992 | Razavi | 502/152 |
| 5,198,401 | 3/1993 | Turner et al. | 502/155 |
| 5,223,467 | 6/1993 | Razavi | 502/152 |
| 5,223,468 | 6/1993 | Razavi | 502/152 |

FOREIGN PATENT DOCUMENTS

| | | |
|---|---|---|
| 200351A2 | 11/1986 | European Pat. Off. . |
| 423100A2 | 4/1991 | European Pat. Off. . |
| 426637A2 | 5/1991 | European Pat. Off. . |
| 426638A2 | 5/1991 | European Pat. Off. . |
| 427696A2 | 5/1991 | European Pat. Off. . |
| 427697A2 | 5/1991 | European Pat. Off. . |
| 468651A2 | 1/1992 | European Pat. Off. . |

OTHER PUBLICATIONS

Breslow and Newburg, *J. Am. Chem. Soc.*, 1959, vol. 81, pp. 81–86.

(Continued on next page.)

*Primary Examiner*—Asok Pal
*Attorney, Agent, or Firm*—M. Susan Spiering; W. G. Muller

[57] ABSTRACT

Ionic catalyst compositions can be prepared by combining two components. The first component is a bis(cyclopentadienyl) Group IV-B metal complex containing at least one ligand which will combine irreversibly with the second component or at least a portion thereof such as a cation portion thereof. The second component comprises a cation which will irrevesibly react with at least one ligand on the Group IV-B metal complex and a non-coordinating anion. The combination of the two components produces an ionic catalyst composition comprising a cationic bis(cyclopentadienyl) Group IV-B metal complex which has a formal coordination number of 3 and a 4+ valence charge and the aforementioned non-coordinating anion. The anion is (i) labile and can be displaced by an olefin, diolefin or acetylenically unsaturated monomer; (ii) has a molecular diameter about or greater than 4 angstroms; (iii) forms stable salts with reducible Lewis acids and protonated Lewis bases; (iv) has a negative charge delocalized over the framework on the anion or within the core thereof; (v) is not a reducing or oxidizing agent; and (vi) is a relatively poor nucleophile. These ionic catalyst compositions can be used to polymerize α-olefins, diolefins and/or acetylenically unsaturated monomers, either alone or in combination, to polymers and copolymers.

15 Claims, 14 Drawing Sheets

OTHER PUBLICATIONS

Long and Breslow, *J. Am. Chem. Soc.*, 1960, vol. 82, pp. 1953–1957.

Dyachkovskii, *Vysokomool. Soyed.*, 1965, vol. 7, pp. 114–115.

Dyachkovskii, Shilova and Shilov, *J. Polym. Sci.* Part C, 1967 pp. 2333–2339.

Eisch et al. *J. Am. Chem. Soc.*, 1985, vol. 107, pp. 7219–7221.

Gianetti, Nicoletti & Mazzochi, *J. Polym. Sci., Polym. Chem.* 1985 vol. 23, pp. 2117–2133.

Ewen et al., *J. Am. Chem. Soc.*, 1987 vol. 109, pp. 6544–6545.

Bochmann & Wilson, *J. Chem. Soc. Chem. Comm.* 1986, pp. 1610–1611.

Jordan et al., JACS, 1986, vol. 108, pp. 7410–7411 no month available.

Jordan et al., JACS, 1986 vol. 108, pp. 1718–1719 no month available.

HIGH FIELD ¹H NMR

FIG. 3  HIGH FIELD TWO DIMENSIONAL NMR:
$^1H$-$^{13}C$ HETERONUCLEAR
CORRELATION SPECTROSCOPY

HIGH FIELD $^{13}$C NMR

HIGH FIELD $^{13}C$ NMR

HIGH FIELD $^{13}$C NMR

IONIC METALLOCENE CATALYST COMPOSITIONS

This is a continuation-in-part of U.S. patent application Ser. No. 737,611 filed Jul. 30, 1991, now U.S. Pat. No. 5,178,401, which is in turn a continuation-in-part of U.S. Ser. No. 555,977 filed Jun. 19, 1990, now abandoned, which is in turn a continuation-in-part of U.S. Ser. No. 133,480 filed Dec. 22, 1987, now abandoned, which is in turn a continuation-in-part of U.S. Ser. No. 008,800 filed Jan. 30, 1987, now abandoned and U.S. Ser. No. 133,052 filed Dec. 22, 1987, now abandoned which is in turn a continuation-in-part of U.S. Ser. No. 011,471 filed Jan. 30, 1987, now abandoned.

FIELD OF THE INVENTION

This invention relates to catalyst compositions, to a method for preparing such catalyst compositions, to a method of using such catalysts and to products produced with such catalyst compositions. More particularly, this invention relates to compositions, comprising ionic metallocene catalyst compositions which are active to polymerize olefins, diolefins and/or acetylenically unsaturated monomers to homopolymer and copolymer products.

BACKGROUND OF THE INVENTION

Soluble Ziegler-Natta type catalysts for the polymerization of olefins are well known in the art. Generally, these catalysts comprise a Group IV-B metal compound and a metal alkyl cocatalyst, particularly an aluminum alkyl cocatalyst. A subgenus of such catalysts is that wherein the Group IV-B metal component comprises a bis(cyclopentadienyl) Group IV-B metal compound (i.e.—a "metallocene"), particularly a titanium compound, in combination with an aluminum alkyl cocatalyst. While speculation remains concerning the actual structure of the active catalyst species of this subgenus of soluble Ziegler-Natta type olefin polymerization catalysts, it appears generally accepted that the structure of the catalytically active species is a Group IV-B metal cation in the presence of a labile stabilizing anion. This is a theory advocated by Breslow and Newburg, and Long and Breslow, in their respective articles in *J. Am. Chem. Soc.*, 1959, Vol. 81, pp. 81–86, and *J. Am. Chem. Soc.*, 1960, Vol. 82, pp. 1953–1957. As there indicated, studies have suggested that the catalytically active species is a titanium-alkyl complex or a species derived therefrom when a titanium compound; viz., bis(cyclopentadienyl)titanium dihalide, and an aluminum alkyl are used as a catalyst or catalyst precursor. The presence of ions, all being in equilibrium, when a titanium compound is used was also suggested by Dyachkovskii, *Vysokomol. Soyed.*, 1965, Vol. 7, pp. 114–115 and by Dyachkovskii, Shilova and Shilov, *J. Polymer. Sci., Part C*, 1967, pp. 2333–2339. That the active catalyst species is a cation complex when a titanium compound is used, was further suggested by Eisch et al., *J. Am. Chem. Soc.*, 1985, vol. 107, pp. 7219–7221.

While the foregoing articles teach or suggest that the active catalyst species is an ion pair wherein the Group IV-B metal component is present as a cation, all of the articles teach the use of a cocatalyst comprising a Lewis acid either to form or to stabilize the active ionic catalyst species. The active catalyst is, apparently, formed through a Lewis acid-Lewis base reaction of two neutral components (the metallocene and the aluminum alkyl), leading to an equilibrium between a neutral catalytically inactive adduct and the active catalyst ion pair. As a result of this equilibrium, there is a competition for the anion which must be present to stabilize the active cation catalyst species. This equilibrium is, of course, reversible and such reversal deactivates the active catalyst species. Further, many, if not all, of the Lewis acids heretofore contemplated for use in soluble Ziegler-Natta type catalyst systems are chain transfer agents and, as a result, prevent effective control of the product polymer molecular weight and molecular weight distribution. Still further, the catalyst systems heretofore proposed do not generally facilitate incorporation of a significant amount of a plurality of different monomers or random distribution of such monomers when used in copolymerization processes, particularly α-olefin copolymerization processes.

The aforementioned metallocene catalyst systems are not highly active, nor are they generally active when the Group IV-B metal is zirconium or hafnium. More recently, however, active Ziegler-Natta type catalysts have been found which are formed when bis(cyclopentadienyl) compounds of the Group IV-B metals, including zirconium and hafnium, are combined with alumoxanes. As is well known, these systems, particularly those employing a zirconocene, offer several distinct advantages, including much higher activities than the aforementioned bis(cyclopentadienyl)titanium catalysts and the production of polymers with narrower molecular weight distributions than those from conventional Ziegler-Natta catalysts. Achiral bis(cyclopentadienyl)hafnium compounds, hafnocenes, used with alumoxane cocatalysts have offered few, if any, advantages when compared to analogous titanocenes or zirconocenes with respect to catalyst activity, polymer molecular weights, or extent or randomness of comonomer incorporation. Giannetti, Nicoletti, and Mazzochi, *J. Polym. Sci., Polym. Chem.*, 1985, Vol. 23, pp. 2117–2133, claim that the ethylene polymerization rates of hafnocenes are five to ten times slower than those of similar zirconocenes while there is little difference between the two metallocenes in the molecular weight of the polyethylene formed from them. European Patent Application No. 200,351 A2 (1986) suggests that in the copolymerization of ethylene and propylene there is little difference between titanocenes, zirconocenes and hafnocenes either in polymer molecular weights and molecular weight distributions or in ability to incorporate propylene randomly. Recently, however, Ewen et al. disclosed in *J. Am. Chem. Soc.*, 1987, Vol. 109, pp. 6544–6545, that chiral hafnocenes used with an alumoxane cocatalyst give isotactic polypropylene of higher molecular weight than that obtained from analogous chiral zirconocenes. In light of the deficiencies of the metallocene catalyst systems heretofore contemplated, a need still exists for an improved metallocene catalyst system which: (1) permits better control of polymer product's molecular weight and molecular weight distribution; (2) is not subject to activation equilibrium, and (3) does not require the use of an undesirable excess of the cocatalyst. The need for a catalyst system which will facilitate the production of higher molecular weight polymeric products and facilitate incorporation of a larger amount of comonomer into a copolymer is also believed to be readily apparent.

SUMMARY OF THE INVENTION

This invention provides improved ionic metallocene catalyst compositions which are useful in the polymerization of olefins, diolefins and/or acetylenically unsaturated monomers. This invention provides a method for preparing such improved catalyst compositions. The improved catalysts are not subject to ion equilibrium reversal deactivation and permit better control of the product polymer molecular weight and molecular weight distribution. The improved catalysts, particularly certain hafnium containing catalysts, yield relatively high molecular weight polymers, yield copolymers containing relatively large amounts of a plurality of comonomers which are also distributed in a manner at least approaching randomness, and provide polymeric products having relatively narrow molecular weight distributions.

The catalyst composition comprises a Group IV-B metal cation and a non-coordinating anion, which composition is represented by one of the general formulae:

$$\{[(A-Cp)MX_1]^+\}_d[B']^{d-} \quad (1)$$

$$\{[(A-Cp)MX_5L']^+\}_d[B']^{d-} \quad (2)$$

wherein:

(A—Cp) is either (Cp)(Cp') or Cp—A'—Cp'; Cp and Cp' are the same or different cyclopentadienyl rings substituted with from zero to five substituent groups S, each substituent group S being, independently, a radical group which is a hydrocarbyl, substituted-hydrocarbyl, halocarbyl, substituted-halocarbyl, hydrocarbyl-substituted organometalloid, halocarbyl-substituted organometalloid and halogen radicals or Cp and Cp' are cyclopentadienyl rings in which any two adjacent S groups are joined forming a $C_4$ to $C_{20}$ ring to give a saturated or unsaturated polycyclic cyclopentadienyl ligand; and A' is a bridging group restricting rotation of the Cp and Cp' rings;

M is titanium, zirconium or hafnium;

L' is a neutral Lewis base;

$X_1$ is a hydride radical, hydrocarbyl radical, substituted-hydrocarbyl radical, halocarbyl radical, substituted-halocarbyl radical, hydrocarbyl-substituted organometalloid radical or halocarbyl-substituted organometalloid radical;

$X_5$ is a hydride radical, hydrocarbyl radical or substituted-hydrocarbyl radical, hydrocarbyl-substituted organometalloid radical or halocarbyl-substituted organometalloid radical, which radical may optionally be covalently bonded to both M and L'; and B' is a chemically stable, non-nucleophilic anionic complex having a molecular diameter about or greater than 4 angstroms; and d is an integer representing the charge of B'.

The improved catalysts are prepared by combining at least two components. The first component is a bis(cyclopentadienyl) derivative of a Group IV-B metal compound containing at least one ligand which will combine with the second component or at least a portion thereof such as a cation portion thereof. The second component is an ion-exchange compound comprising a cation which will irreversibly react with at least one ligand contained in said Group IV-B metal compound (first component) and a non-coordinating anion.

The cation portion of the second component may comprise a wide variety species which are known to abstract anionic ligands bound to early transition metals including Bronsted acids such as protons or protonated Lewis bases or, reducable Lewis acids such as ferricinium, tropylium, triphenylcarbenium or silver cations.

The key to proper anion design for the second component requires that the anionic complex is labile and stable toward reactions with the cationic metallocene in the final catalyst species. We have discovered that anions which are stable toward reactions with water or Bronsted acids and which do not have acidic protons located on the exterior of the anion (i.e. anionic complexes which do not react with strong acids or bases) possess the stability necessary to qualify as a stable anion for the catalyst system. The properties of the anion which are important for maximum lability include overall size, and shape (i.e. large radius of curvature), and nucleophilicty. Using these guidelines one can use the chemical literature to choose non-coordinating anions which can serve as components in the catalyst system. In general, suitable anions for the second component may be any stable and bulky anionic complex having the following molecular attributes: 1) the anion should have a molecular diameter about or greater than 4 angstroms; 2) the anion should form stable salts with reducible Lewis Acids and protonated Lewis bases; 3) the negative charge on the anion should be delocalized over the framework of the anion or be localized within the core of the anion; 4) the anion should be a relatively poor nucleophile; and 5) the anion should not be a powerful reducing or oxidizing agent. Anions meeting these criteria—such as polynuclear boranes, carboranes, metallacarboranes, polyoxoanions and anionic coordination complexes are well described in the chemical literature. Upon combination of the first and second components, the cation of the second component reacts with one of the ligands of the first component, thereby generating an ion pair consisting of a Group IV-B metal cation and the aforementioned anion, which anion is compatible with and noncoordinating towards the Group IV-B metal cation formed from the first component. The anion of the second compound must be capable of stabilizing the Group IV-B metal cation without interfering with the Group IV-B metal cation's ability to function as a catalyst and must be sufficiently labile to permit displacement by an olefin, diolefin or an acetylenically unsaturated monomer during polymerization. For example, Kochmann and Wilson have reported in *J. Chem. Soc., Chem. Comm.*, 1986, pp. 1610–1611) that bis(cyclopentadienyl)titanium dimethyl reacts with tetrafluoroboric acid to form bis(cyclopentadienyl)-titanium methyl tetrafluoroborate. The anion is, however, insufficiently labile to be displaced by ethylene in large part due to its small overall molecular size.

DETAILED DESCRIPTION OF THE INVENTION

Figure 1:
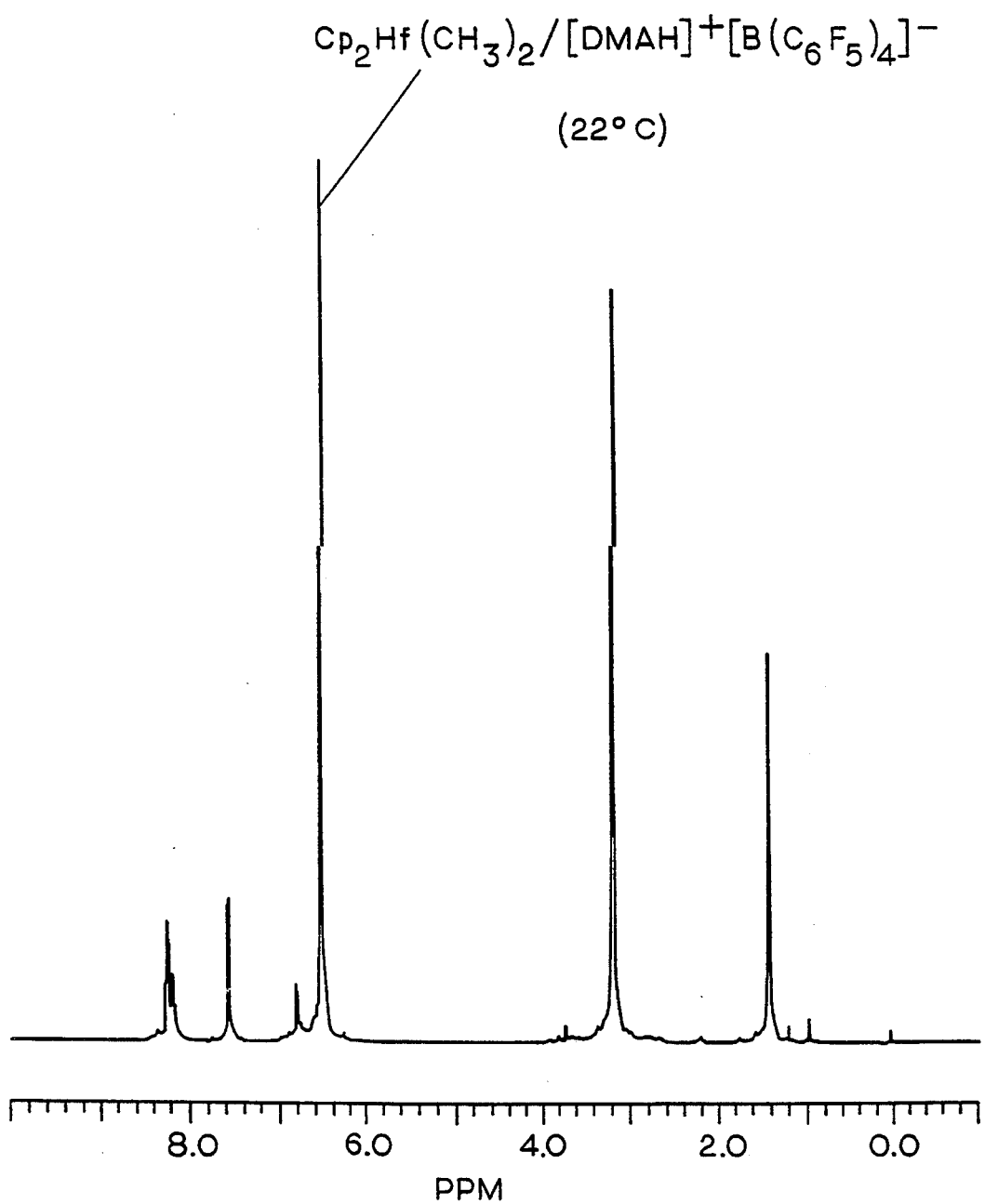
FIG. 1 is a room temperature $^1H$ NMR spectrum of the bottom phase collected from the reaction of bis(cyclopentadienyl)hafnium dimethyl [$Cp_2HfMe_2$] with one equivalent of N,N-dimethylanilium tetra(pentafluorophenyl)boron [HDMA][B(pfp)$_4$].

The improved catalysts can be prepared by combining at least one first compound which is a bis(cyclopentadienyl) derivative of a metal of the Group IV-B of the Periodic Table of the Elements containing at least one ligand which will react with an acidic hydrogen atom (i.e., proton) and at least one second compound which is a salt comprising a cation capable of donating a proton which will irreversibly combine with said at least one ligand (substituent) liberated by said Group IV-B metal compound and an anion which is either a single coordination complex comprising a plurality of lipophilic radicals covalently coordinated to and shielding a central formally charge-bearing metal or metalloid atom or an anion comprising a plurality of boron atoms such as polyhedral boranes, carboranes and metallacarboranes, which anion is both bulky and labile, compatible with and noncoordinating toward the Group IV-B metal cation formed from the first component, and capable of stabilizing the Group IV-B metal cation without interfering with said Group IV-B metal cation's ability to polymerize α-olefins, diolefins and/or acetylenically unsaturated monomers.

All reference to the Periodic Table of the Elements herein shall refer to the Periodic Table of the Elements, published by CRC Press, Inc., 1984. Also, any reference to a Group or Groups shall be to the Group or Groups as reflected in this Periodic Table of the Elements. Hereafter, the bis(cyclopentadienyl) Group IV-B metal compound may be referred to as a "metallocene"; wherein the metal is titanium the compound may be referred to as a "titanocene"; when zirconium as a "zirconocene"; and when hafnium as a "hafnocene." The second component, which by reaction with the metallocene activates it to a catalytically active complex, may hereafter be referred to as an "activator compound."

The second component, or activator compound, is comprised of a cation and an anion, which anion is compatible with and non-coordinating to the Group IV-B metal cation formed by reaction between the first and second components.

As used herein with reference to the initial activator compound or the ionic composition which results from the reaction of a metallocene and an activator compound, the recitation "compatible noncoordinating anion" means an anion which either does not coordinate to the Group IV-B metal cation or which is only weakly coordinated to said cation thereby remaining sufficiently labile to be displaced by a neutral Lewis base. The recitation "compatible noncoordinating anion" specifically refers to an anion which when functioning as a stabilizing anion in the catalyst system of this invention does not transfer an anionic substituent or fragment thereof to Group IV-B metal cation thereby forming a neutral four coordinate metallocene and a neutral metal or metalloid byproduct. Compatible anions are anions which are not degraded to neutrality when the initially formed complex decomposes. The recitation "metalloid" as used herein, includes nonmetals such as boron, phosphorus and the like which exhibit semi-metallic characteristics.

The Group IV-B metal compounds; i.e., titanium, zirconium and hafnium metallocene compounds, useful as first compounds in the preparation of the improved catalyst of this invention are bis(cyclopentadienyl) derivatives of titanium, zirconium and hafnium in which one or both of the two non-cyclopentadienyl ligands bonded to the metal center are hydrolyzable by water. In general, useful titanocenes, zirconocenes and hafnocenes may be represented by the following general formulae:

(A—Cp)MX$_1$X$_2$        (3)

(A—Cp)MX'$_1$X'$_2$        (4)

(A—Cp)ML        (5)

(Cp')(CpR)MX$_1$        (6)

Wherein "Cp" represents a cyclopentadienyl radical which may be substituted or unsubstituted, and:

(A—Cp) is either (Cp)(Cp') or Cp—A'—Cp' and Cp and Cp' are the same or different cyclopentadienyl ring substituted with from zero to five substituent groups S, and each substituent group S is, independently, a radical which can be hydrocarbyl, substituted-hydrocarbyl, halocarbyl, substituted-halocarbyl, hydrocarbyl-substituted organometalloid, halocarbyl-substituted organometalloid, or halogen radicals (the size of the radicals need not be limited to maintain catalytic activity, however, generally the radical will be a C$_1$ to C$_{20}$ radical) or Cp and Cp' are a cyclopentadienyl ring in which any two adjacent R groups are joined forming a C$_4$ to C$_{20}$ ring to give a saturated or unsaturated polycyclic cyclopentadienyl ligand such as indenyl, tetrahydroindenyl, fluorenyl, or octahydrofluorenyl and A' is a bridging group which restricts rotation of the two Cp-groups; M is titanium, zirconium or hafnium; L is an olefin, diolefin or aryne ligand; X$_1$ and X$_2$ are, independently, selected from the group consisting of hydride radicals, hydrocarbyl radicals, halocarbyl, substituted-hydrocarbyl radicals, substituted-halocarbyl radicals, hydrocarbyl-substituted organometalloid radicals, halocarbyl-substituted organometalloid radicals; $X'_1$ and $X'_2$ are joined and bound to the metal atom to form a metallacycle, in which the metal atom, $X'_1$ and $X'_2$ form a hydrocarbocyclic ring containing from about 3 to about 20 carbon atoms; and S is a substituent, preferably a hydrocarbyl substituent, on one of the cyclopentadienyl radicals which is also bound to the metal atom.

Each carbon atom in the cyclopentadienyl radical ("Cp") may be, independently, unsubstituted or substituted with the same or a different radical group which is a hydrocarbyl, substituted-hydrocarbyl, halocarbyl, substituted-halocarbyl hydrocarbyl radicals in which adjacent substituents are joined to form a ring of 4 to 10 or more carbon atoms, hydrocarbyl- and halocarbyl-substituted organometalloid radicals, and halogen radicals. Suitable hydrocarbyl and substituted-hydrocarbyl radicals, which may be substituted for at least one hydrogen atom in a cyclopentadienyl radical include straight and branched alkyl radicals, cyclic hydrocarbon radicals, alkyl-substituted cyclic hydrocarbon radicals, aryl substituted radicals and alkyl aryl-substituted radicals. Similarly, and when $X_1$ and/or $X_2$ is a hydrocarbyl or substituted-hydrocarbyl radical, each may, independently, contain from 1 to about 20 carbon atoms and be a straight or branched alkyl radical, a cyclic hydrocarbyl radical, an alkyl-substituted cyclohydrocarbyl radical, an aryl radical or an alkyl alkyl-substituted radical. Suitable organometalloid radicals include mono-, di- and trisubstituted organometalloid radicals. More particularly, suitable organometalloid radicals include trimethylsilyl, triethylsilyl, ethyldimethylsilyl, methyldiethylsilyl, triphenylgermyl, trimethylgermyl and the like.

Illustrative, but not limiting examples of bis(cyclopentadienyl)zirconium compounds which may be used in the preparation of the improved catalyst of this invention are dihydrocaryl-substituted bis(cyclopentadienyl)zirconium compounds such as bis(cyclopentadienyl)zirconium dimethyl, bis(cyclopentadienyl)zirconium diethyl, bis(cyclopentadienyl)zirconium dipropyl, bis(cyclopentadienyl)zirconium dibutyl, bis(cyclopentadienyl)zirconium diphenyl, bis(cyclopentadienyl)zirconium dineopentyl, bis(cyclopentadienyl)zirconium di(m-tolyl), bis(cyclopentadienyl)zirconium di(p-tolyl) and the like; (monohydrocarbyl-substituted cyclopentadienyl)zirconium compounds such as (methylcyclopentadienyl) (cyclopentadienyl) and bis(methylcyclopentadienyl)zirconium dimethyl, (ethylcyclopentadienyl) (cyclopentadienyl) and bis(ethylcyclopentadienyl)zirconium dimethyl, (propylcyclopentadienyl) (cyclopentadienyl) and bis(propylcyclopentadienyl)zirconium dimethyl, (n-butylcyclopentadienyl) (cyclopentadienyl) and bis(n-butylcyclopentadienyl)zirconium dimethyl, (t-butylcyclopentadienyl) (cyclopentadienyl) and bis(t-butylcyclopentadienyl)zirconium dimethyl, (cyclohexylmethylcyclopentadienyl) (cyclopentadienyl) and bis(cyclohexylmethylcyclopentadienyl)zirconium dimethyl, (benzylcyclopentadienyl)(cyclopentadienyl) and bis(benzylcyclopentadienyl)zirconium dimethyl, (diphenylmethylcyclopentadienyl)(cyclopentadienyl) and bis(diphenylmethylcyclopentadienyl)zirconium dimethyl, (methylcyclopentadienyl)(cyclopentadienyl) and bis(methylcyclopentadienyl)zirconium dihydride, (ethylcyclopentadienyl)(cyclopentadienyl) and bis(cyclopentadienyl)zirconium dihydride, (propylcyclopentadienyl)(cyclopentadienyl) and bis(propylcyclopentadienyl)zirconium dihydride, (n-butylcyclopentadienyl)(cyclopentadienyl) and bis(n-butylcyclopentadienyl)zirconium dihydride, (t-butylcyclopentadienyl)(cyclopentadienyl) and bis(t-butylcyclopentadienyl)zirconium dihydride, (cyclohexylmethylcyclopentadienyl)(cyclopentadienyl) and bis(cyclohexylmethylcyclopentadienyl)zirconium dihydride, (benzylcyclopentadienyl)(cyclopentadienyl) and bis(benzylcyclopentadienyl)zirconium dihydride, (diphenylmethylcyclopentadienyl)(cyclopentadienyl) and bis(diphenylmethylcyclopentadienyl)zirconium dihydride and the like; (polyhydrocarbyl-substituted-cyclopentadienyl)zirconium compounds such as (dimethylcyclopentadienyl)(cyclopentadienyl) and bis(dimethylcyclopentadienyl)zirconium dimethyl, (trimethylcyclopentadienyl)(cyclopentadienyl) and bis(trimethylcyclopentadienyl)zirconium dimethyl, (tetramethylcyclopentadienyl)(cyclopentadienyl) and bis(tetramethylcyclopentadienyl)zirconium dimethyl, (permethylcyclopentadienyl)(cyclopentadienyl) and bis(permethylcyclopentadienyl)zirconium dimethyl, (ethyltetramethylcyclopentadienyl)(cyclopentadienyl) and bis(ethyltetramethylcyclopentadienyl)zirconium dimethyl, (indenyl)(cyclopentadienyl) and bis(indenyl)zirconium diemthyl, (dimethylcyclopentadienyl)(cyclopentadienyl) and bis(dimethylcyclopentadienyl)zirconium dihydride, (trimethylcyclopentadienyl)(cyclopentadienyl) and bis(trimethylcyclopentadienyl)zirconium dihydride, (tetramethylcyclopentadienyl)(cyclopentadienyl) and bis(tetramethylcyclopentadienyl)zirconium dihydride, (permethylcyclopentadineyl) and bis(permethylcyclopentadienyl)zirconium dihydride, (ethyltetramethylcyclopentadienyl)(cyclopentadienyl) and bis(ethyltetramethylcyclopentadienyl)zirconium dihydride, (indenyl)(cyclopentadienyl) and bis(indenyl)zirconium dihydride, (metalloid hydrocarbyl-substituted cyclopentadienyl)zirconium compounds such as (trimethylsilylcyclopentadienyl)(cyclopentadienyl) and bis(trimethylsilylcyclopentadienyl)zirconium dimethyl, (trimethylgermylcyclopentadienyl)(cyclopentadienyl) and bis(trimethylgermylcyclopentadienyl)zirconium dimethyl, (trimethylplumbylcyclopentadieny)(cyclopentadienyl) and bis(trimethylplumbylcyclopentadienyl)zirconium dimethyl, (trimethylsilylcyclopentadienyl)(cyclopentadienyl) and bis(trimethylsilylcyclopentadienyl)zirconium dihydride, (trimethylgermylcyclopentadienyl)(cyclopentadienyl) and bis(trimethylgermycyclopentadienyl)zirconium dihydride, (trimethylstannylcyclopentadienyl)(cyclopentadienyl) and bis(trimethylstannycyclopentadienyl)zirconium dihydride, (trimethylplumbylcyclopentadienyl)(cyclopentadienyl) and bis(trimethylplumbylcyclopentadienyl)zirconium dihydride and the like; (halocarbyl-substituted-cyclopentadienyl)zirconium compounds such as (trifluoromethylcyclopentadienyl)(cyclopentadienyl) and bis(trifluoromethylcyclopentadienyl)zirconium dimethyl (trifluoromethylcyclopentadienyl)(cyclopentadienyl) and bis(trifluoromethylcyclopentadienyl)zirconium dihydride and the like; silyl-substituted bis(cyclopentadienyl) zirconium compounds such as bis(cyclopentadienyl) (trimethylsilyl)(methyl)zirconium, bis(cyclopentadienyl)(triphenylsilyl)(methyl)zirconium, bis(cyclopentadienyl)[tris(dimethylsilyl)silyl](methyl)-zirconium, bis(cyclopentadienyl)(trimethylsilyl)(tris(trimethylsilyl)methyl)zirconium, bis(cyclopentadienyl)(trimethylsilylbenzyl) and the like; (bridged-cyclopentadienyl)zirconium compounds such as methylene bis(cyclopentadienyl)zirconium dimethyl, methylene(cyclopentadienyl)zirconium dimethyl, ethylene bis(cyclopentadienyl)zirconium dimethyl, dimethylsilyl bis(cyclopentadienyl)zirconium dihydride, ethylene bis(cyclopentadienyl)zirconium dihydride and dimethylsilyl bis(cyclopentadienyl)zirconium dihydride and the like; chiral and $C_2$-symmetion compounds; "zirconacycles"; asymmetrically bridged-dicyclopentadienyl compounds such as methylene(cyclopentadienyl)( 1-fluorenyl)zirconium dihydride, isopropyl(cyclopentadienyl)(1-fluorenyl)zirconium dimethyl, isopropyl(cyclopentadienyl)(1-octahydro-fluorenyl)zirconium dimethyl, dimethylsilyl(methylcyclopentadienyl)(1-fluorenyl) zirconium dihydride, methylene(cyclopentadienyl(tetramethylcyclopentadienyl)zirconium dimethyl and the like: racemic and meso isomers of symmetrically bridged substituted dicyclopentadienyl compounds such as ethylenebis(indenyl)zirconium dimethyl, dimethylsilybis(indenyl)zirconium dimethyl, ethylenebis(tetrahydroindenyl)zirconium dimethyl, dimethylsilybis(3-trimethylsilylcyclopentadienyl)zirconium dihydride and the like; zirconacycles such as bis(pentamethylcyclopentadienyl)zirconacyclobutane, bis(pentamethylcyclopentadienyl)zirconacyclopentane, bis(cyclopentadienyl)zirconaindane, 1-bis(cyclopentadienyl)zircona-3-dimethylsilacyclobutane and the like; olefin, diolefin and aryne ligand substituted bis(cyclopentadienyl)zirconium compounds such as bis(cyclopentadienyl)(1,3-butadiene)zirconium, bis(cyclopentadienyl)(2,3-dimethyl-1,3-butadiene)zirconium, bis(pentamethylcyclopentadienyl)(benzyne)zirconium and the like; (hydrocarbyl)(hydride) bis(cyclopentdienyl)zirconium compounds such as bis(pentamethylcyclopentadienyl)zirconium (phenyl) (hydride), bis(pentamethylcyclopentadienyl)zirconium (methyl)(hydride) and the like; and bis(cyclopentadienyl)zirconium compounds in which a substituent on the cyclopentadienyl radical is bound to the metal such as (pentamethylcyclopentadienyl)(tetramethylcyclopentadienylmethylene)zirconium hydride, (pentamethylcyclopentadienyl)(tetramethylcyclopentadienylmethylene)zirconium phenyl and the like.

A similar list of illustrative bis(cyclopentadienyl) hafnium and bis(cyclopentadienyl)titanium compounds could be made, but since the lists would be nearly identical to that already presented with respect to bis(cyclopentadienyl)zirconium compounds, such lists are not deemed essential to a complete disclosure. Other bis(cyclopentadienyl)hafnium compounds and other bis(cyclopentadienyl)titanium compounds as well as other bis(cyclopentadienyl)zirconium compounds which are useful in the catalyst compositions of this invention will, of course, be apparent to those skilled in the art.

Compounds useful as a second component, or as the activator compound, in the preparation of the catalyst of this invention comprise a cation, preferably are a Bronsted acid capable of donating a proton, and a compatible noncoordinating anion containing a single coordination complex comprising a charge-bearing metal or metalloid core which is relatively large (bulky), capable of stabilizing the active catalyst species (the Group IV-B cation) which is formed when the metallocene and activator compounds are combined, and said anion is sufficiently labile to be displaced by olefinic, diolefinic and acetylenically unsaturated substrates or other neutral Lewis bases such as ethers, nitriles and the like. Any metal or metalloid capable of forming a coordination complex which is resistant to degradation by water (or other Bronsted or Lewis Acids) may be used or contained in the anion of the second activator compound. Suitable metals include, but are not limited to, aluminum, gold, platinum and the like. Suitable metalloids include, but are not limited to, boron, phosphorus, silicon and the like.

Compounds containing anions which comprise coordination complexes containing a single metal or metalloid atom are, of course, well known and many, particularly compounds containing a single boron atom in the anion portion, are available commercially. In light of this, salts containing anions comprising a coordination complex containing a single boron atom are preferred. In general, the second activator compounds useful in the preparation of the catalysts of this invention may be represented by the following general formula:

$$[(L'-H)^+]_d[(M')^{m+}Q_1Q_2\ldots Q_n]^{d-} \quad (7)$$

wherein:

$L'$ is a neutral Lewis base;

H is a hydrogen atom;

$(L'-H)$ is a Bronsted acid;

$M'$ is a metal or metalloid;

$Q_1$ to $Q_n$ are, independently, bridged or unbridged hydride radicals, dialkylamido radicals, alkoxide and aryloxide radicals, hydrocarbyl and substituted-hydrocarbyl radicals, halocarbyl and substituted halocarbyl radicals, and hydrocarbyl- and halocarbyl-substituted organometalloid radicals and any one, but not more than one, of $Q_1$ to $Q_n$ may be a halide radical;

m is an integer representing the formal valence charge of $M'$;

n is the total number of ligands Q; and d is an integer representing the total charge on the anion.

Second activator compounds comprising boron which are particularly useful in the preparation of catalysts of this invention are represented by the following general formula:

$$[L'-H]^+[BAr_1Ar_2X_3X_4]^- \quad (8)$$

wherein:

$L'$ is a neutral Lewis base;

H is a hydrogen atom;

$[L'-H]^+$ is a Bronsted acid;

B is boron in a valence state of 3+;

$Ar_1$ and $Ar_2$ are the same or different aromatic or substituted-aromatic hydrocarbon radicals and may be linked to each other through a stable bridging group; and $X_3$ and $X_4$ are, independently, hydride radicals, halide radicals, with the proviso that only $X_3$ or $X_4$ will be halide, hydrocarbyl radicals, substituted-hydrocarbyl radicals, halocarbyl radicals, substituted-halocarbyl radicals, hydrocarbyl- and halocarbyl-substituted organometalloid radicals, dialkylamido radicals, and alkoxy and aryloxy radicals.

In general, $Ar_1$ and $Ar_2$ may, independently, be any aromatic or substituted-aromatic hydrocarbon radical. Suitable aromatic radicals include, but are not limited to, phenyl, naphthyl and anthracenyl radicals. Suitable substituents on useful substituted-aromatic hydrocarbon radicals, include, but are not necessarily limited to, hydrocarbyl radicals, organometalloid radicals, alkoxy radicals, alkylamido radicals, fluoro and fluorohydrocarbyl radicals and the like such as those useful as $X_3$ or $X_4$. The substituent may be ortho, meta or para, relative to carbon atom bonded to the boron atom. When either or both $X_3$ and $X_4$ are a hydrocarbyl radical, each may be the same or a different aromatic or substituted-aromatic radical as are $Ar_1$ and $Ar_2$, or the same may be a straight or branched alkyl, alkenyl or alkynyl radical, a cyclic hydrocarbon radical or an alkylsubstituted cyclic hydrocarbon radical. $X_3$ and $X_4$ may also, independently, be alkoxy or dialkylamido radicals, hydrocarbyl radicals and organometalloid radicals and the like. As indicated supra, $Ar_1$ and $Ar_2$ may be linked to each other. Similarly, either or both of $Ar_1$ and $Ar_2$ could be linked to either $X_3$ or $X_4$. Finally, $X_3$ and $X_4$ may also be linked to each other through a suitable bridging group.

Illustrative, but not limiting, examples of boron compounds which may be used as an activator component in the preparation of the improved catalysts of this invention are trialkyl-substituted ammonium salts such as triethylammonium tetra(phenyl)boron, tripropylammonium tetra(phenyl)boron, tri(n-butyl)ammonium tetra(phenyl)boron, trimethylammonium tetra(p-tolyl)boron, trimethylammonium tetra(o-tolyl)boron, tributylammonium tetra(pentafluorophenyl)boron, tripropylammonium tetra(o,p-dimethylphenyl)boron, tributylammonium tetra(m,m-dimethylphenyl)boron, tributylammonium tetra(p-trifluoromethylphenyl)boron, tributylammonium tetra(pentafluorophenyl)boron, tri(n-butyl)ammonium tetra(o-tolyl)boron and the like; N,N-dialkyl anilinium salts such as N,N-dimethylanilinium tetra(phenyl)boron, N,N-diethylanilinium tetra(phenyl)boron, N,N-2,4,6-pentamethylanilinium tetra(phenyl)boron and the like; dialkyl ammonium salts such as di-(isopropyl)ammonium tetra(pentafluorophenyl)boron, dicyclohexylammonium tetra(phenyl)boron and the like; and triaryl phosphonium salts such as triphenylphosphonium tetra(phenyl)boron, tri(methylphenyl)phosphonium tetra(phenyl)boron, tri(dimethylphenyl)phosphonium tetra(phenyl)boron and the like.

Similar lists of suitable compounds containing other metals and metalloids which are useful as activator components could be made, but such lists are not deemed necessary to a complete disclosure. In this regard, it should be noted that the foregoing list is not intended to be exhaustive and other boron compounds that would be useful as well as useful compounds containing other metals or metalloids would be readily apparent, from the foregoing general equations, to those skilled in the art.

In general, and while most metallocenes identified above may be combined with most activator compounds identified above to produce an active olefin polymerization catalyst, it is important to continued polymerization operations that either the metal cation initially formed from the metallocene, or a decomposition product thereof, be a relatively stable catalyst. It is also important that the anion of the activator compound be chemically stable and bulky. Further, when the cation of the activator component is a Bronsted acid, it is important that the acidity of the activator compound be sufficient, relative to the metallocene, to facilitate the needed proton transfer. Conversely, the basicity of the metal complex must also be sufficient to facilitate the needed proton transfer. In general, metallocenes in which the non-cyclopentadienyl ligands can be hydrolyzed by aqueous solutions can be considered suitable metallocenes for forming the catalysts described herein, because water (our reference Bronsted acid) is a weaker acid than the ammonium ions used as cation in our preferred ion-exchange reagents. This concept allows on of ordinary skill in the art to choose useful metallocene components because stability to water is a basic chemical property easily determined experimentally or by using the chemical literature.

The chemical reactions which occur upon combination of a first metallocene compound with a second activator compound may be represented by reference to the general formulae set forth herein as follows:

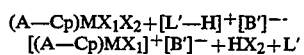

or

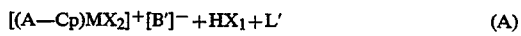 (A)

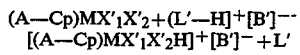

or

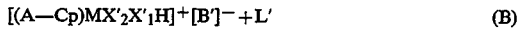 (B)

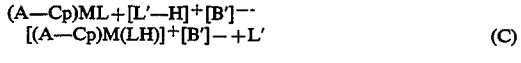 (C)

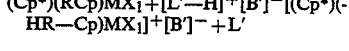

or

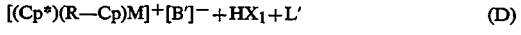 (D)

In the foregoing reaction equations, the letters A-D correspond to the numbers 1-4, respectively, set forth in combination with the general equations for useful metallocene compounds. B' represents a compatible ion corresponding to the general formulae outlined in formulae 7 and 8 above. When the metallocene and activator components used to prepare the improved catalysts of the present invention are combined in a suitable solvent or diluent, all or a part of the cation of the activator (the acidic proton) combines with one of the substituents on the metallocene compound. In the case where the metallocene component has a formula corresponding to that of general formula 3, a neutral compound is liberated, which neutral compound either remains in solution or is liberated as a gas. In this regard, it should be noted that if either $X_1$ or $X_2$ in the metallocene component is a hydride, hydrogen gas may be liberated. Similarly, if either $X_1$ or $X_2$ is a methyl radical, methane may be liberated as a gas. In the cases where the first component has a formula corresponding to those of general formulae 4, 5 or 6 (optional), one of the substituents on the metallocene component is protonated but no substituent is liberated. In general, the rate of formation of the products in the foregoing reaction equations will vary depending upon the choice of the solvent, the acidity of the $[L'—H]^+$ selected, the particular $L'$, the anion, the temperature at which the reaction is completed and the particular cyclopentadienyl derivative of the metal selected.

As indicated, the improved catalyst compositions of the present invention will, preferably, be prepared in a suitable solvent or diluent. Suitable solvents or diluents include any of the solvents known in the prior art to be useful as solvents in the polymerization of olefins, diolefins and acetylenically unsaturated monomers. Suitable solvents, then, include, but are not necessarily limited to, straight and branched-chain hydrocarbons such as isobutane, butane, pentane, hexane, heptane, octane and the like; cyclic and alicyclic hydrocarbons such as cyclohexane, cycloheptane, methylcyclohexane, methylcycloheptane and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexane, 3-methyl-1-pentene, 4-methyl-1-pentene, 1,4-hexadiene, 1-octene, 1-decene and the like. Suitable solvents further include basic solvents which are not generally useful as polymerization solvents when conventional Ziegler-Natta type polymerization catalysts are used such as chlorobenzene.

As before discussed, the active catalyst species of the catalyst of this invention is relatively stable and is not subject to the ion equilibrium deactivation as are alumoxane cocatalyzed metallocene catalyst systems. Unlike metallocene-alumoxane catalyst systems wherein, to obtain a practical level of catalyst productivity it is generally required to use an amount of alumoxane, measured as aluminum atom, to provide a ratio of Al:transition metal well in excess of 1000:1; catalysts of this invention which are highly productive may be prepared at ratios of metallocene to activator of 10:1 to about 1:1, preferably about 3:1 to 1:1.

In the process of characterizing the reaction products isolated from the reaction of a wide variety of first and second components we have identified several classes of catalytically active ionic complexes. In all cases the initial activation reaction produces a three coordinate hydrido- or hydrocarbyl-cation as indicated in the general formulae set forth in A, B, C and D, but the structure of the final catalyst species depends on such factors as (1) the metallocene used and the degree to which the cyclopentadienyl ligands of such metallocenes are substituted; (2) the nature of the anion moiety of the second or activator compound and the degree and type of substitution on such anions; (3) the nature of the cation moiety of the second or activator compound—particularly the molecular size of the neutral Lewis base which is liberated from such cation upon loss therefrom of a proton; and (4) the ratios at which the metallocene and activator compound are employed. Each of the structurally distinct ionic complexes described below represent a general class of useful and novel catalytically active species which are commonly produced in the reaction of first and second components described in this invention.

With respect to the combination of a metallocene and an activator compound to form a catalyst of this invention, it should be noted that the two compounds combined for preparation of the active catalyst must be selected so as to avoid transfer of a fragment of the activator compound anion, particularly an aryl group, to the metallocene metal cation, thereby forming a catalytically inactive species. When anions consisting of hydrocarbyl anions are used, there are several means of preventing anion degradation and formation of inactive species. One method is to carry out the protonolysis process in the presence of small Lewis bases such as tetrahydrofuran. Discrete complexes can be isolated from these reactions, but the Lewis base is insufficiently labile to be displaced readily by olefin monomers, resulting in, at best, catalysts of very low activity. Another method of avoiding deleterious anion degradation is by steric hindrance. Anions of the second component which contain aryl groups can be made more resistant to degradation by introducing substituents in the ortho positions of the phenyl rings. While active metallocene polymerization catalysts can be generated by this method, the complex reaction chemistry often prevents characterization of the catalytically active species. Steric hindrance can also result form substitutions on the cyclopentadienyl rings of the metallocene component. Hence, wherein the metallocene used is a bis(peralkyl-substituted cyclopentadienyl) Group IVB metal compound, the high degree of substitution on the cyclopentadienyl ring creates sufficient bulkiness that the Lewis base generated by the protonolysis reaction not only cannot coordinate to the metal but also polyarylborate anions without substituents on the aryl rings do not transfer aryl fragments to generate catalytically inactive species. Under these conditions, as illustrated by Examples 1, 4, 10 and 22, the most stable species formed is a zwitterion.

This behavior is best exemplified in a metallocene comprised of bis(peralkylcyclopentadienyl) ligands wherein a tetraphenyl borate is used as the anion of the activator compound. For example, the reaction of Cp*$_2$ZrMe$_2$ (where Cp=Me$_5$Cp) and [Bu$_3$NH]+[B(Ph$_4$)]− (where Ph, =phenyl or para-alkylphenyl with hydrogen or an alkyl group in the para-position) in toluene gives [Cp*$_2$ZrMe]+[B(Ph)$_4$] which is unstable and decomposes by loss of methane to give a single catalytically active product. The deep red product has been fully characterized by NMR spectroscopy and single crystal x-ray diffraction. The general structure of this zwitterionic catalyst of this type is shown below:

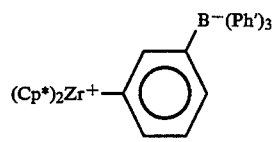

wherein:

Cp* is a peralkyl-substituted cyclopentadienyl radical wherein each of said alkyl substitutions may be the same or a different alkyl radical, preferably the same or a different C$_1$–C$_6$ alkyl radical, most preferably the same or a different C$_1$–C$_4$ alkyl radical; B is boron; Zr is zirconium; Ph' is a phenyl or alkyl-substituted phenyl radical and each of the 3 Ph's may be the same or different, the alkyl substitutions preferably being C$_1$–C$_6$, most preferably C$_1$–C$_4$.

Addition of excess hydrogen gas to a toluene solution containing the above-identified pentamethyl-substituted cyclopentadienyl zwitterionic catalyst causes a rapid reaction as evidenced by a color change from red to yellow, and, in concentrated solutions, the formation of a yellow precipitate. Removal of hydrogen from the system regenerates the original zwitterionic catalyst in high yield. It is believed that the reaction of hydrogen with the zwitterionic catalyst leads to the formation of [Cp*$_2$ZrH]+[B(Ph')$_4$]. The reversible nature of this reaction along with other spectroscopic evidence suggests that the hydride cation is in chemical equilibrium with the zwitterionic species.

Consistent with the foregoing, stable polymerization catalysts have been prepared when bis(permethylcyclopentadienyl) zirconium dimethyl has been reacted with tri(n-butyl)ammonium tetra(phenyl)boron, tri(n-butyl)ammonium tetra(p-tolyl)boron and tri(n-butyl)ammonium tetra(p-ethylphenyl)boron. A stable polymerization catalyst has also been prepared when bis(ethyltetramethylcyclopentadienyl)zirconium dimethyl was reacted with tri(n-butyl)ammonium tetra(p-tolyl)boron. In each of these cases, the stable polymerization catalyst was prepared by adding the reactants into a suitable aromatic solvent at a temperature within the range from about 0C. to about 100C. It appears clear that stable zwitterionic polymerization catalysts can also be prepared using bis(perhydrocarbylcyclopentadienyl)zirconium dialkyls and dihydrides in combination with ammonium salts of an unsubstituted or p-substituted-tetra(aryl)boron anion. Another means of rendering the anion of the activator compound more resistant to degradation is afforded by fluoride substitution, especially perfluoro substitution, in the anion thereof. One class of suitable non-coordinating anions can be represented by the formula $[B(C_6F_5)_3Q]^-$ where Q is a monoanionic non-bridging radical as described above. The preferred anion of the activator compound of this invention, tetra(pentafluorophenyl)boron, hereafter referred to for convenience by the notation $[B(C_6F_5)_4]^-$, or $[B(pfp)_4]^-$, is virtually impervious to degradation and can be used with a much wider range of metallocene cations, including those without substitution on the cyclopentadienyl rings, than anions comprising hydrocarbyl radicals. The tetra(pentafluoro) boron anion is illustrated below:

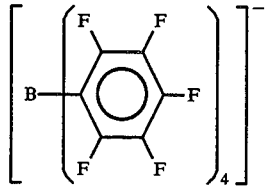

Since this anion has little or no ability to coordinate to the metallocene cation and is not degraded by the metallocene cation, structures of the ion-pair metallocene catalysts using the $[B(pfp)_4]^-$ anion depend on steric hindrance of substituents on the cyclopentadienyl rings of metallocene, the nature of the cation of the activator component, the Lewis base liberated from the protonolysis reaction, and the ratio at which the metallocene and activator component are combined. If Lewis bases other than that liberated from the proton transfer process are present, they may complex to the metal to form modified catalysts of this invention. One such modified catalyst can be represented by the formula:

$$\{[[(A\text{—}Cp)M_1X_1]\text{—}X_7\text{—}[(A\text{—}Cp)'M_2X_6]]^+\}_d[B']^{d-} \qquad (9)$$

wherein:
(A—Cp) and (A—Cp)' are the same or different;
M₁ and M₂ are the same or different metal selected from the Group consisting of titanium, zirconium and hafnium;
X₁ and X₆ are independently selected from the group consisting of hydride radicals, hydrocarbyl radicals, substituted-hydrocarbyl radicals, halocarbyl radicals, substituted-halocarbyl radicals, hydrocarbyl- and halocarbyl-substituted organometalloid radicals; and
X₇ is a derivative of an X₁ or X₆ radical bridging M₁ and M₂.

When the cation of the activator compound is one which, upon the proton reaction with the substituent of the metallocene, liberates a small neutral Lewis base, like N,N-dimethylaniline (DMA), steric hinderance usually does not prevent coordination of the neutral Lewis base to the metallocene cation.

Accordingly, there is a competition between DMA and unreacted metallocene as to which will coordinate to and stabilize the metallocene cation formed by the proton reaction between the metallocene and the activator compound. The most stable catalyst species that can be formed therefore depends upon the ratio of metallocene (M) to activator compound (A). At a ratio of M:A of 1:1, upon completion of the proton reaction there remains no unreacted metallocene. The only neutral Lewis base remaining available to coordinate to and stabilize the metallocene cation is DMA. In such circumstances the species formed can be represented by one of three general formulae which are subsets of the general formula 2 of $[(A\text{—}Cp)MX_5L']^+$ as defined above:

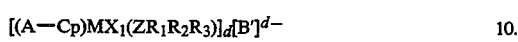

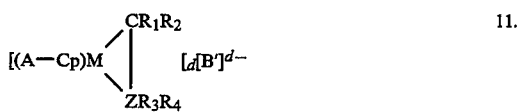

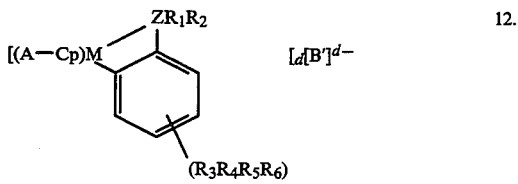

wherein:
Z is a Group V-A element; and
R₁ to R₆ are independently hydride, hydrocarbyl, substituted-hydrocarbyl, halocarbyl, substituted-halocarbyl, hydrocarbyl-substituted organometalloid, halocarbyl-substituted organometalloid, or halide radicals.

Three distinct examples of such complexes are illustrated below, where each R' and R" is the same or different S substituent as defined above and x and y are, independently, integers from zero to five:

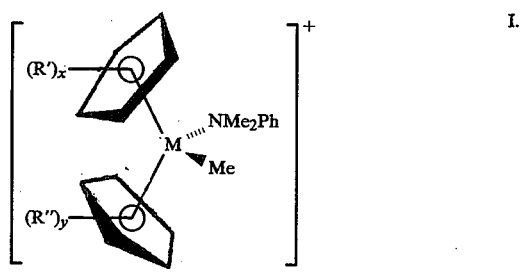

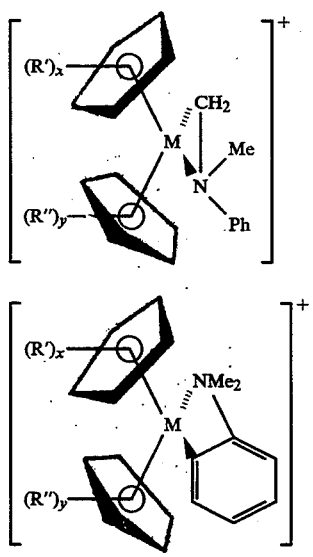

It is important to note that cations [(A—Cp)MX₅L']+ wherein X₅ and L' are covalently bonded to each other (as in II and III) may be useful as catalysts for the modification of X₅L'-substrates. This may be especially useful when A—Cp is a stereochemically rigid chiral ligand set.

In cases where the activator compound is used in less than a 1:1 stoichiometric amount relative to the metallocene, a corresponding amount of unreacted metallocene remains available in the system. The unreacted metallocene, although an extremely weak Lewis base, is nevertheless a Lewis base comparable in strength to DMA. The unreacted metallocene which remains in the system serves as a Lewis base source to coordinate to and stabilize the metallocene cation formed. In circumstances wherein unreacted metallocene serves to stabilize the metallocene cation, the catalytic species formed is of the general structure:

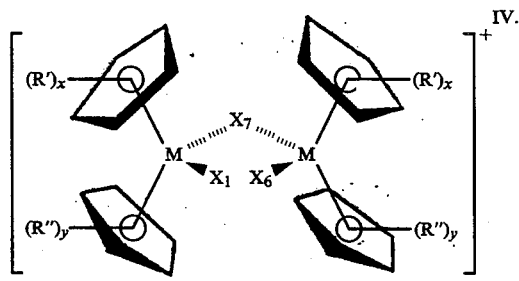

Accordingly, wherein the metallocene is used in excess relative to the activator compound, and the activator compound is one the cation portion of which is a small protonated Lewis base such as N,N-dimethylaniline, the relative amounts of catalyst species of formula II and IV is dictated by the equilibrium conditions then prevailing. At metallocene to activator compound ratios of 1:1 the species of formula I first forms which, at room temperature may slowly decompose to give active catalysts with structures like those of formulae II and III.

As the ratio of metallocene to activator is increased from 1:1, the equilibrium will increasingly comprise amounts of species IV. The partition between the amounts of species II and IV formed at steady state conditions appears to follow classic equilibrium behavior. The equilibrium constants will depend on the metal, the number and type of substitutions on the cyclopentadienyl rings and the relative basicity of the Lewis base L'. In order to prepare a catalyst composition which is essentially composed solely of species IV it is necessary to use an excess of metallocene to activator of greater than 1:1, preferably from about 3:1 or greater.

Wherein a catalyst is prepared using an activator compound comprising a cation of large molecular dimensions, such as a tri(n-butyl)ammonium cation, the neutral Lewis base liberated from the activator compound upon reaction with the metallocene, namely tri-n-butylamine, is too bulky to coordinate with the resulting transition metal cation of the metallocene. Accordingly, an active catalyst species in the nature of a neutral Lewis base coordinated metallocene cation cannot form. Instead, the active catalyst species initially formed is exclusively a metallocene cation dimerically coordinated with a neutral metallocene molecule, as illustrated by structure IV. The dimeric coordination occurs through a divalent hydride or through a hydrocarbyl radical at least one carbon atom of which exists in a formal 5-coordinate state. The relative stability of this dimeric catalyst species is in part dependent upon the molar ratio of metallocene to activator compound used in preparing the catalyst. Wherein a metallocene to activator compound ratio of 1:1 is employed, as a metallocene molecule reacts with an activator compound molecule to form a metallocene metal cation, that cation immediately coordinates to the best Lewis base species present in the reaction solution. Since the neutral Lewis base liberated by reaction of the activator compound is too bulky to coordinate with the neutral cation, the next best Lewis base available in solution are unreacted metallocene molecules. Hence a metallocene cation molecule immediately coordinates to an unreacted metallocene molecule to form a relatively stable dimeric species of metallocene cation. In this manner, the full equivalent of metallocene is consumed while only one half of the activator compound equivalence is consumed. Thereafter, in a kinetically slower process, the remaining unreacted one half equivalent of activator compound reacts with the dimeric species of metallocene metal cation to form an intermediate species of structure:

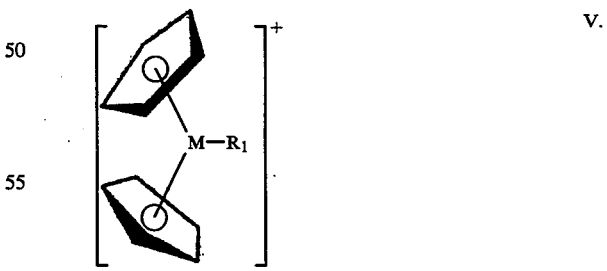

Again, since the neutral Lewis base of Bu₃N liberated by consumption of the activator compound is too bulky to coordinate with Species V, and since there is no longer available in solution any alternative Lewis base capable of stabilizing species V, it quickly decomposes to products whose structures are as yet undetermined but which are still cationic and catalytically active.

In the case of a catalyst prepared at a ratio of from about 2:1 to 3:1, metallocene to activator compound, the dimeric form of catalyst species, species IV, may be essentially exclusively formed, and once formed is relatively stable, having a half life of several hours at room temperature.

When the catalyst is prepared in toluene a rapid reaction occurs yielding a two-phase liquid system. The upper layer is essentially pure toluene while the bottom layer is an air sensitive yellow liquid. Characterization of the catalyst species has been accomplished by an indirect method which involved reacting the yellow catalyst layer with d$_8$-THF to form a d$_8$-THF adduct that is soluble in THF. The catalyst structure has also been characterized by High Field NMR spectroscopy. The $^1$HMR spectrum of the yellow liquid after extraction with d$_8$-THF suggests that DMA which is liberated during activation is coordinated to the metal center to form a stable adduct, [Cp$_2$M(CH$_3$)L'][B(C$_6$F$_5$)$_4$]. This is an unexpected result since tertiary amines are not good ligands for transition metal complexes.

Figure 2:
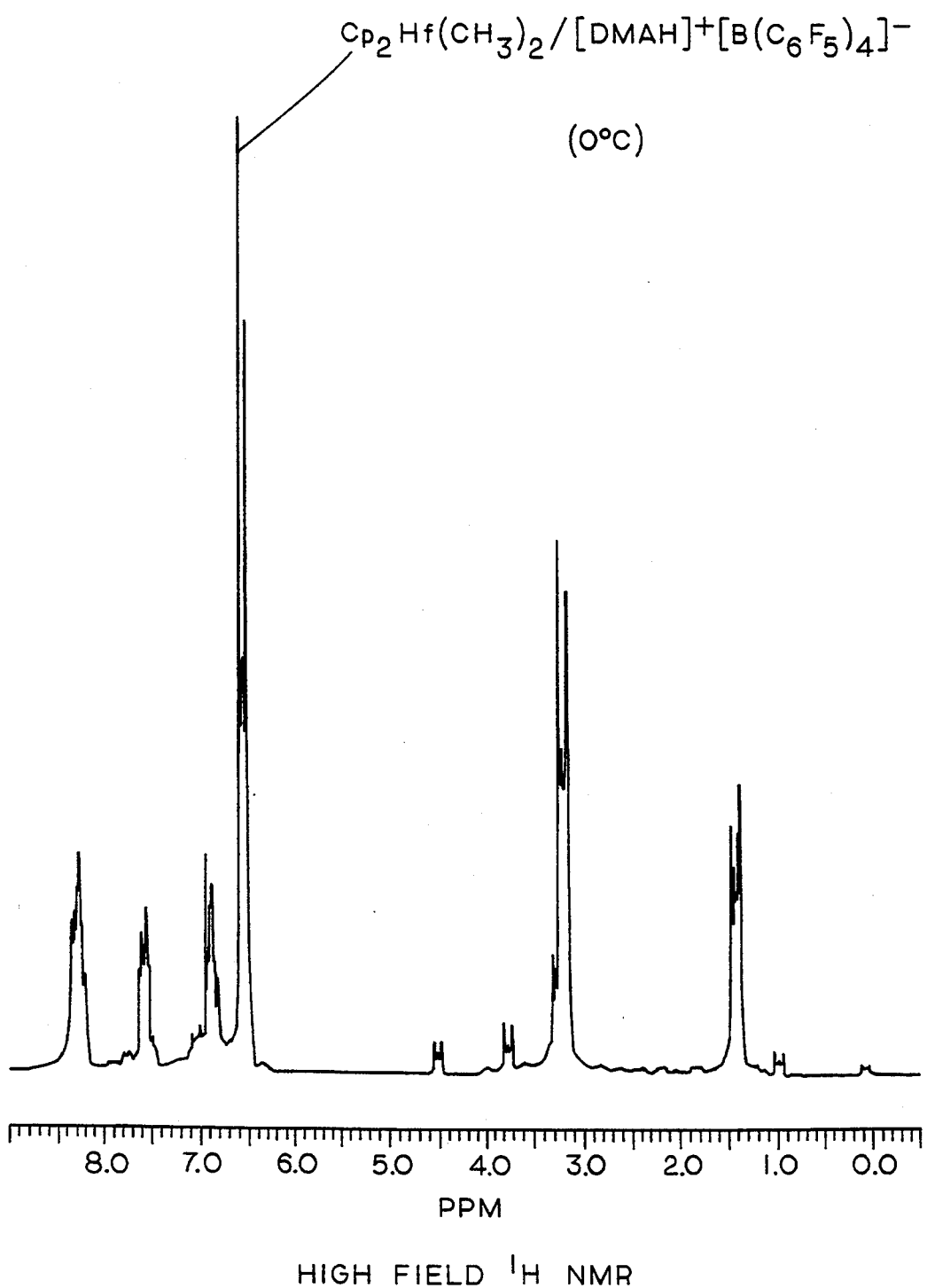
FIG. 2 is a $^1H$ NMR spectrum of the bottom phase, as per FIG. 1, wherein the sample was maintained at 0C.

The reaction of Cp$_2$HfMe$_2$ (where Cp=C$_5$H$_5$, Me=CH$_3$) with one equivalent of [DMAH][B(pfp)$_4$] was carried out in deuterated benzene. The reaction proceeded quickly (5 minutes) to give a two phase system. The top phase is essentially pure d$_6$-benzene, with a yellow bottom phase containing the catalyst and deuterated solvent. The amount of deuterated solvent in the catalyst phase is a thermodynamic property of the system and cannot be raised by adding more solvent. However, the concentration of deuterated solvent is high enough to be used as a lock solvent for NMR experiments. The room temperature $^1$H NMR spectrum of the bottom phase was collected and is shown in FIG. 1. The assignments for the Cp-group (6.49 ppm), the aniline methyl groups (3.14 ppm), and the methyl group bonded to hafnium (1.39 ppm) are based on chemical shift data collected for known model compounds and their relative integrated intensities (e.g. 10:6:3). The sharp signals at 6.49, 3.14, and 1.39 ppm broaden and coalesce into multiplets as the temperature is lowered to 0° C. The low temperature $^1$H NMR (0° C.) spectrum is shown in FIG. 2. The complex appearance of the $^1$H NMR spectrum is due to the presence of rotomeric isomers (different orientations of the coordinated aniline ligand with respect to the metallocene framework of the basic structure—see Structure VII, below. At elevated temperatures the rate rotation about the Hf—N bond increases and the multiple signals observed for the methyl and Cp-signals coalesce into sharp singlets. The spectra demonstrate that the reaction is remarkably clean, producing one type of stable metallocene complex. The fact that the chemical shift of the aniline methyl signal is shifted downfield by 10 ppm relative to free DMA is consistent with coordination of the aniline to the cationic metal center. The chemical shift of the hafnium methyl group (44.5 ppm) is shifted downfield from neutral hafnocene methyl complexes; again, this is consistent with a cationic hafnium center. The B(pfp)$_4^-$ carbon signals have the same pattern and chemical shift as the parent ammonium salt indicating the anion is intact and is not strongly interacting with the cationic metal center. The $^1$H and $^{13}$C NMR data are consistent with the structure shown below:

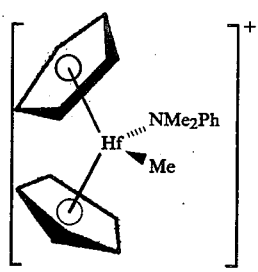

VI.

Figure 3:
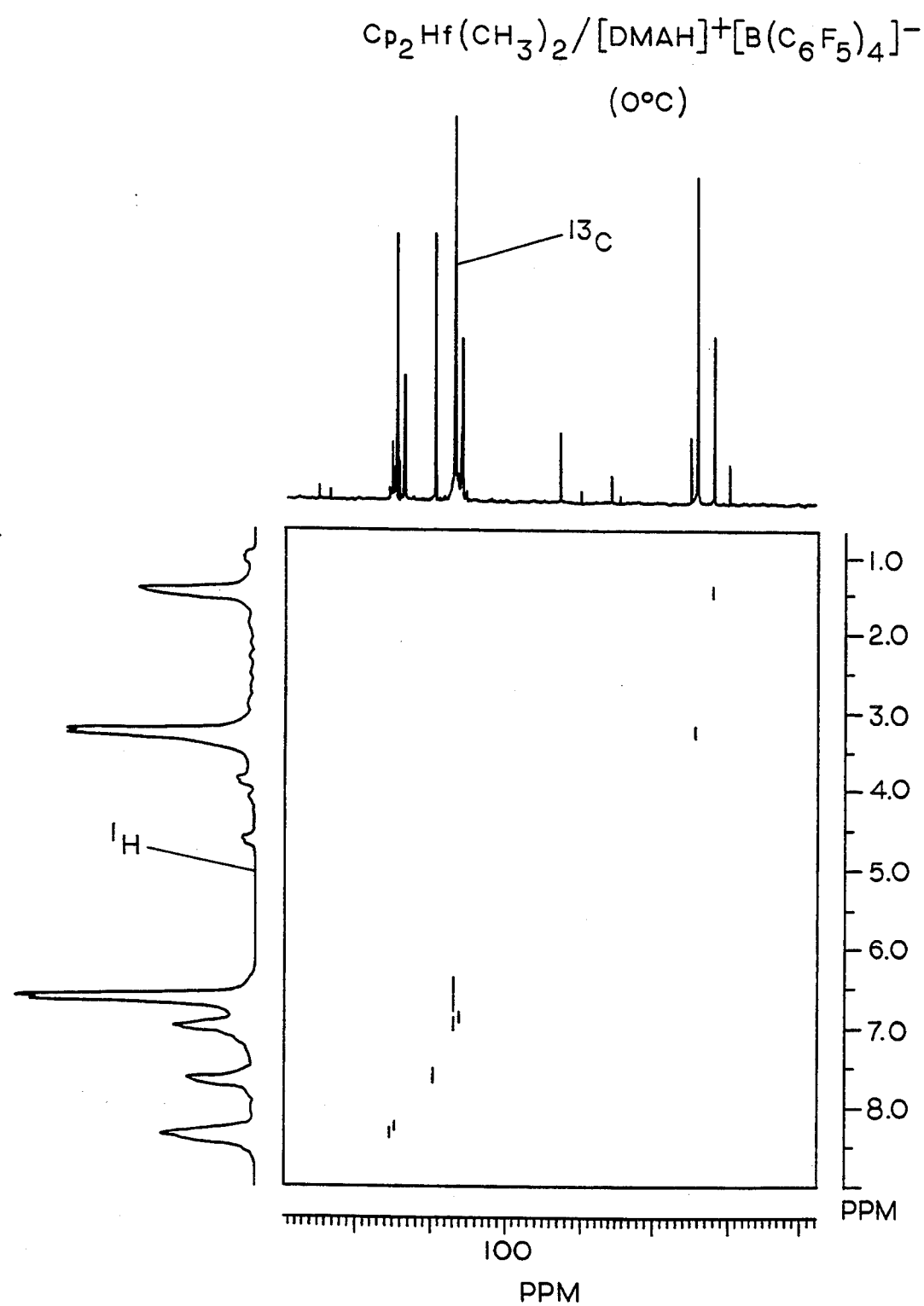
FIG. 3 is a heteroneuclear correlation spectroscopy spectrum, $^1H$-$^{13}C$ COSY, of the bottom phase as per FIG. 1.

Heteronuclear correlation spectroscopy, $^1$H-$^{13}$C COSY, was used to confirm the assignments made. The COSY analysis determines the correlation of $^{13}$C NMR signals to the $^1$H NMR signals. In this spectrum the one dimensional $^{13}$C spectrum appears on the horizontal axis and the 1D $^1$H NMR spectrum appears on the vertical axis (the overall resolution of this spectrum is typically lower than in a 1D spectrum). The 2D COSY spectrum is a contour plot of the intensity of the cross-peaks which occur when the $^1$H and $^{13}$C signals are correlated. Correlation of the proton and carbon resonances indicates that they are directly bonded together. The two dimensional NMR technique requires long acquisition times (typically overnight). For this reason the analysis was carried out at low temperature (0° C.) to minimize thermal decomposition of the catalyst during the acquisition. The 2D COSY of the bottom phase is shown in FIG. 3. The signal assigned to Hf-Me is correlated to the proton signal at 1.4 ppm and the aniline methyl signal is correlated to the proton signal at 3.1 ppm. The three signals of the protonated ring carbons of coordinated DMA at 114, 119, and 130 are correlated to the $^1$H signals at 6.8, 7.5 and 8.2 ppm, respectively. The Cp-ring carbons at 114 ppm are correlated to the $^1$H Cp-signal at 6.5 ppm. Again, these correlations strongly corroborate the structure as assigned in in Structure VII. Note that the $^{13}$C signal of the DMA carbon at 114 ppm overlaps with Cp-carbon signal, but in the COSY spectrum these signals are resolved in the second dimension.

Figure 4:
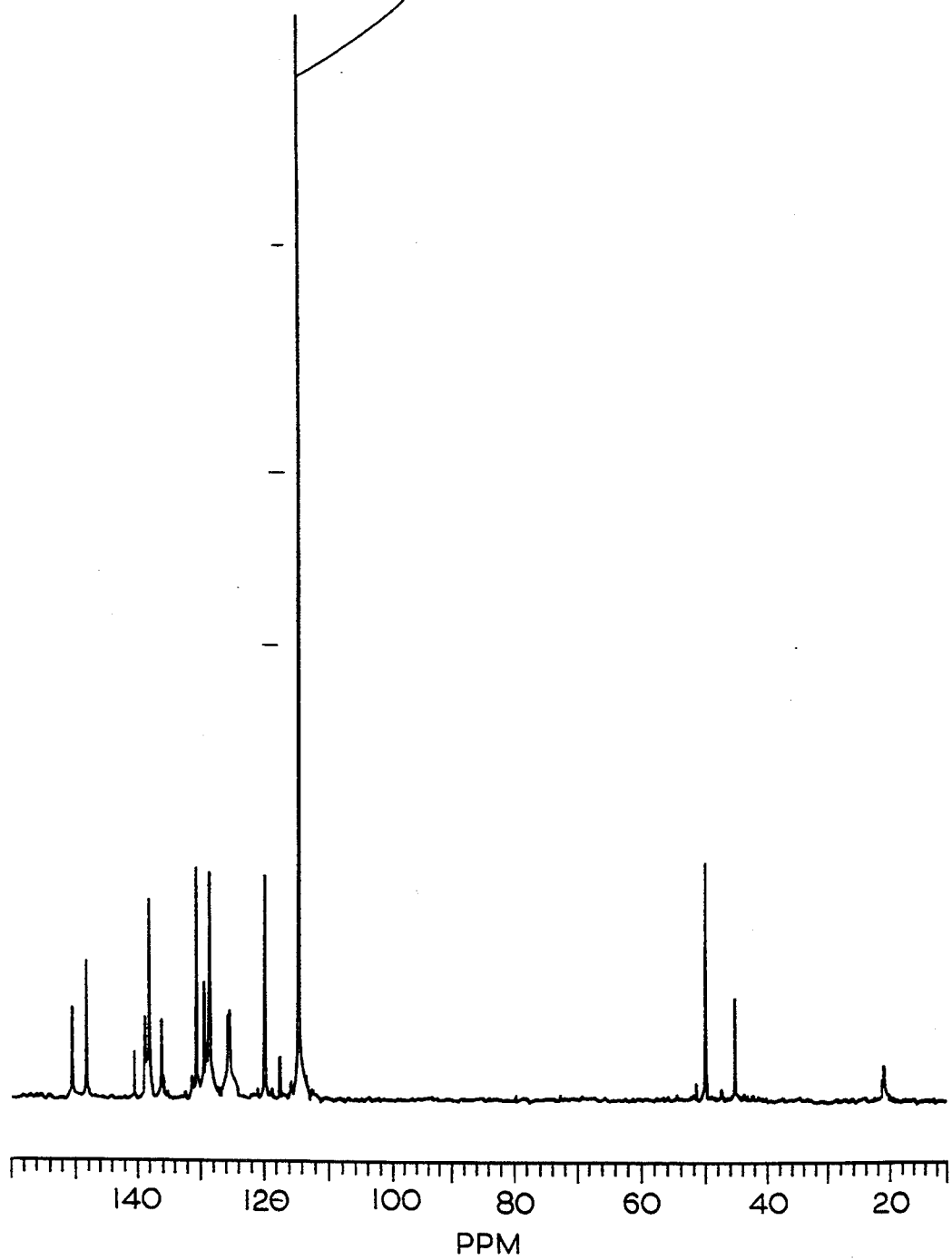
FIG. 4 is a $^{13}$C NMR spectrum of a freshly prepared sample of [Cp$_2$HfMe(DMA)]$^+$[B(pfp)$_4$]$^-$ in d$_8$-toluene.
Figure 5:
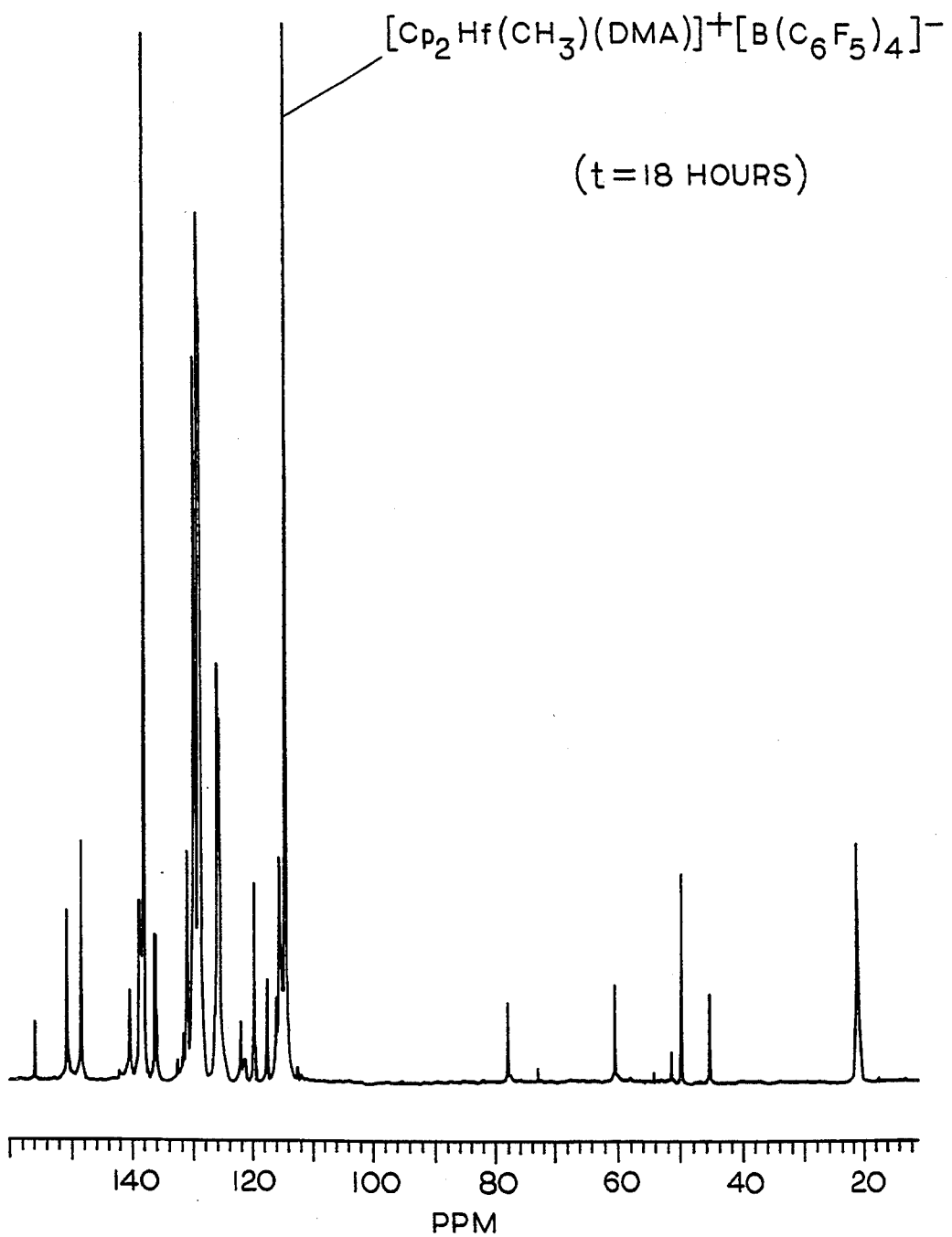
FIG. 5 is a $^{13}$C NMR spectrum of the sample of FIG. 4 after 18 hours at ambient temperature.

The thermal decomposition of the hafnium DMA-adduct [Cp$_2$HfMe(DMA)][B(pfp)$_4$] has been studied. A $^{13}$C NMR spectrum of fresh [Cp$_2$HfMe(DMA)][B(pfp)$_4$] in d$_8$-toluene is shown in FIG. 4. The sample was stored in a N$_2$ atmosphere at ambient temperature, after 18 hours the spectrum shown in FIG. 5 was collected. Integration of a signal assigned to the B(pfp)$_4^-$ anion (the reference) relative to the signal due to the methyl groups on the coordinated DMA ligand on [Cp$_2$HfMe(DMA)][B(pfp)$_4$] was used to estimate the degree of decomposition of the DMA adduct. The estimated half life of [Cp$_2$HfMe(DMA)][B(pfp)$_4$] is 18 hours at ambient temperatures. In the decomposition products it appears that the boron anion has not been destroyed, meaning that the metal remains cationic. Thus the decomposition of [Cp$_2$HfMe(DMA)][B(pfp)$_4$] involves loss of methane and formation of new ionic products. NMR evidence shows that decomposition can give cations where the aniline ligand has been metallated as shown below in Structures VII and VIII.

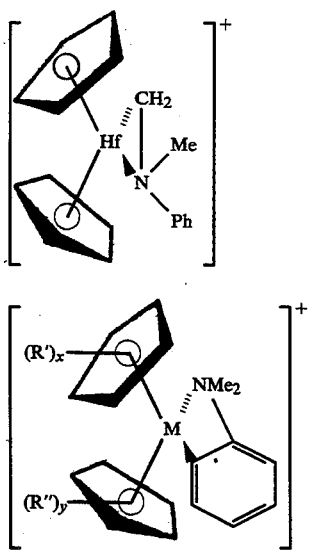

VII.

VIII.

Further possible decomposition products are those wherein, upon loss of methane, the Cp ring and/or the solvent (exemplified by benzene) become metallated as shown below in Structures IX and X. While these species have been not been produced in high yield during thermal decomposition, we have observed clear evidence for their formation in NMR experiments. The structures are catalytically active because they possess the structural features necessary for olefin polymerization: high valent (d⁰), coordinatively unsaturated (formal three coordination), alkyl cations.

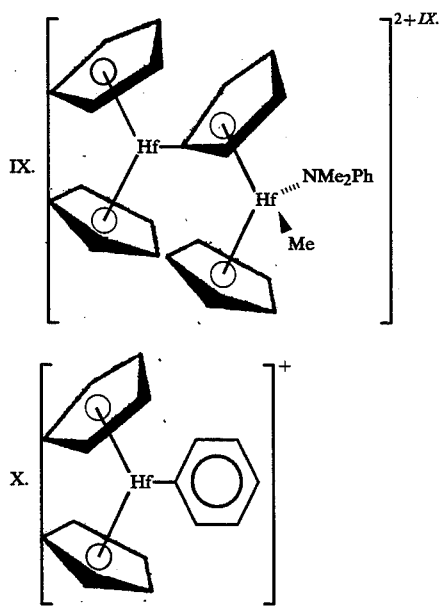

IX.

X.

The decomposition products remain active olefin polymerization catalysts because the basic structure required for catalytic activity remains intact, i.e. three coordinate metal cation with a reactive metal-carbon sigmabond.

Figure 6:
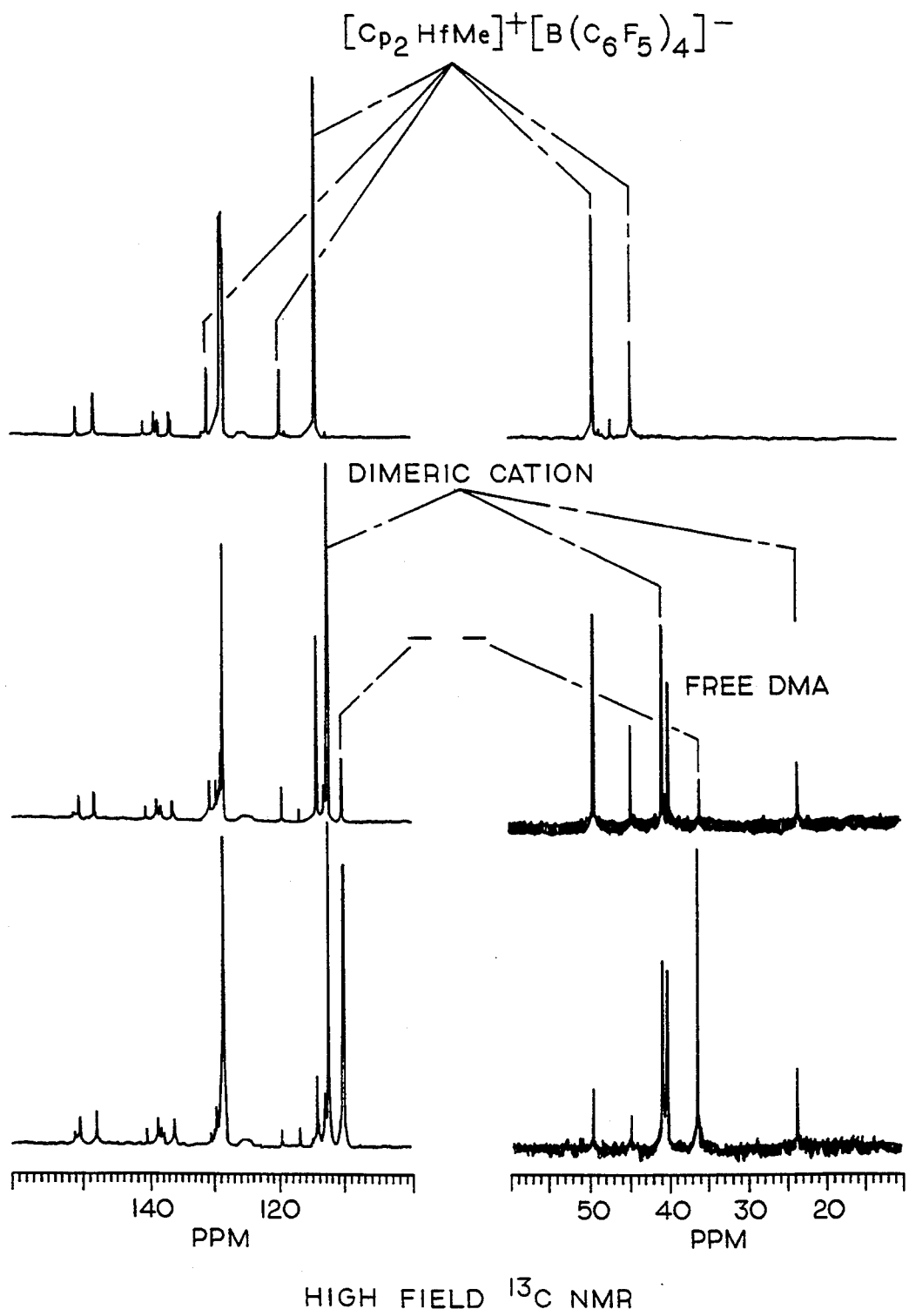
FIG. 6 is a high field $^{13}$C NMR spectra of [Cp$_2$HfMe(DMA)]$^+$[B(pfp)$_4$]$^-$ which has been reacted with zero, one and two equivalents of Cp$_2$HfMe$_2$.

The high field $^{13}C$ NMR spectra of $Cp_2HfMe(DMA)][B(pfp)_4]$ reacted with zero, one and two equivalents of $Cp_2HfMe_2$ are shown in FIG. 6. The NMR data suggests that $Cp_2HfMe_2$ acts as a Lewis base and displaces coordinated DMA to form the dimeric cation shown below in Structure XI.

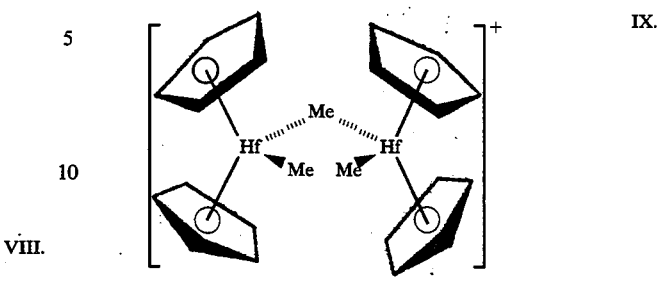

IX.

Signals due to $[Cp_2HfMe(DMA)][B(pfp)_4]$, $Cp_2HfMe_2$ and free DMA have been labeled in FIG. 6. The new signals found at 41 ppm and 23.5 ppm are assigned to the terminal and bridging methyl groups on the dimeric cation; the new signal at 112 ppm is assigned to the four equivalent Cp-rings of the dimeric cation. Further evidence for the formation of the dimeric cation involves its isolation and reaction with THF to give $[Cp_2HfMe(THF)][B(pfp)_4]$ and $Cp_2HfMe_2$ in a 1:1 ratio. That the amount of dimeric cation and free DMA increases as the concentration of $Cp_2HfMe_2$ increases evidences that an equilibrium exists between $Cp_2HfMe(DMA)]$ and the dimeric cation [Structure XI]. The Lewis base strength of DMA and $Cp_2HfMe_2$ are estimated to be very close since the addition of one equivalent of $Cp_2HfMe_2$ gives a nearly 50:50 mixture of the two metallocene cations.

The dimeric cation of Structure XI has been observed, isolated, and characterized and is an active catalyst.

The $^{13}C$ NMR spectrum of the reaction of one equivalent of $[Bu_3NH][B(pfp)_4]$ with $Cp_2HfMe_2$ in $d_6$-benzene shows the presence of the dimeric cation, free $Bu_3N$ and unreacted $[Bu_3NH][B(pfp)_4]$ after 20 minutes at room temperature. After two hours the dimeric cation and unreacted $[Bu_3NH][B(pfp)_4]$ disappeared and the spectrum shows free $Bu_3N$ and several unidentified metallocene signals. The bottom layer was quenched with $d_8$-THF and the $^1H$ NMR spectrum was collected. The spectrum showed $Cp_2HfMe_2$, $Cp_2HfMe(THF-d_8)][B(pfp)_4]$ and $[Bu_3NH][B(pfp)_4]$ in nearly equal molar ratios. Diagram 1 below describes an interpretation of these data.

Diagram 1

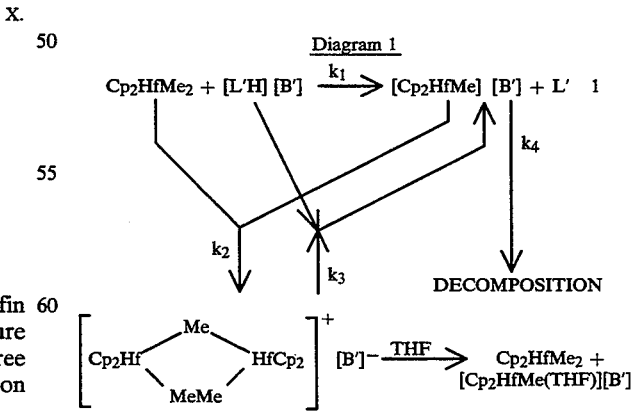

Free $Bu_3N$ is not capable of coordinating to and stabilizing the three coordinate cation 1, and the best Lewis base in solution is unreacted Cp$_2$HfMe$_2$. Cp$_2$HfMe$_2$ and Cp$_2$HfMe][B(pfp)$_4$] react to form the dimeric cation discussed earlier. It has been shown that THF and the dimeric cation react to give equal molar amounts of Cp$_2$HfMe(THF)][B(pfp)$_4$] and Cp$_2$HfMe$_2$ (thus explaining the d$_8$-THF quenching experiment). The rate of formation of 2 from 1 (k$_2$) is fast compared to the rate of decomposition of the three coordinate complex (k$_4$). Furthermore, the rate of protonation of 2 by the unreacted activator must be relatively slow because unreacted activator is observed even after 20 minutes by $^{13}$C NMR. Thus, the first half of equivalent of activator is quickly consumed to form the dimeric cation. The dimeric cation slowly reacts with the remaining activator (k$_3$) to form two equivalents of "naked" cation 1 which decomposes (by reaction with solvent, other cations, the Cp-ligand and/or free amine) since there is no Lewis base in solution capable of stabilizing the system. In the decomposition products the anion is not degraded and the metal center remains cationic.

Figure 7:
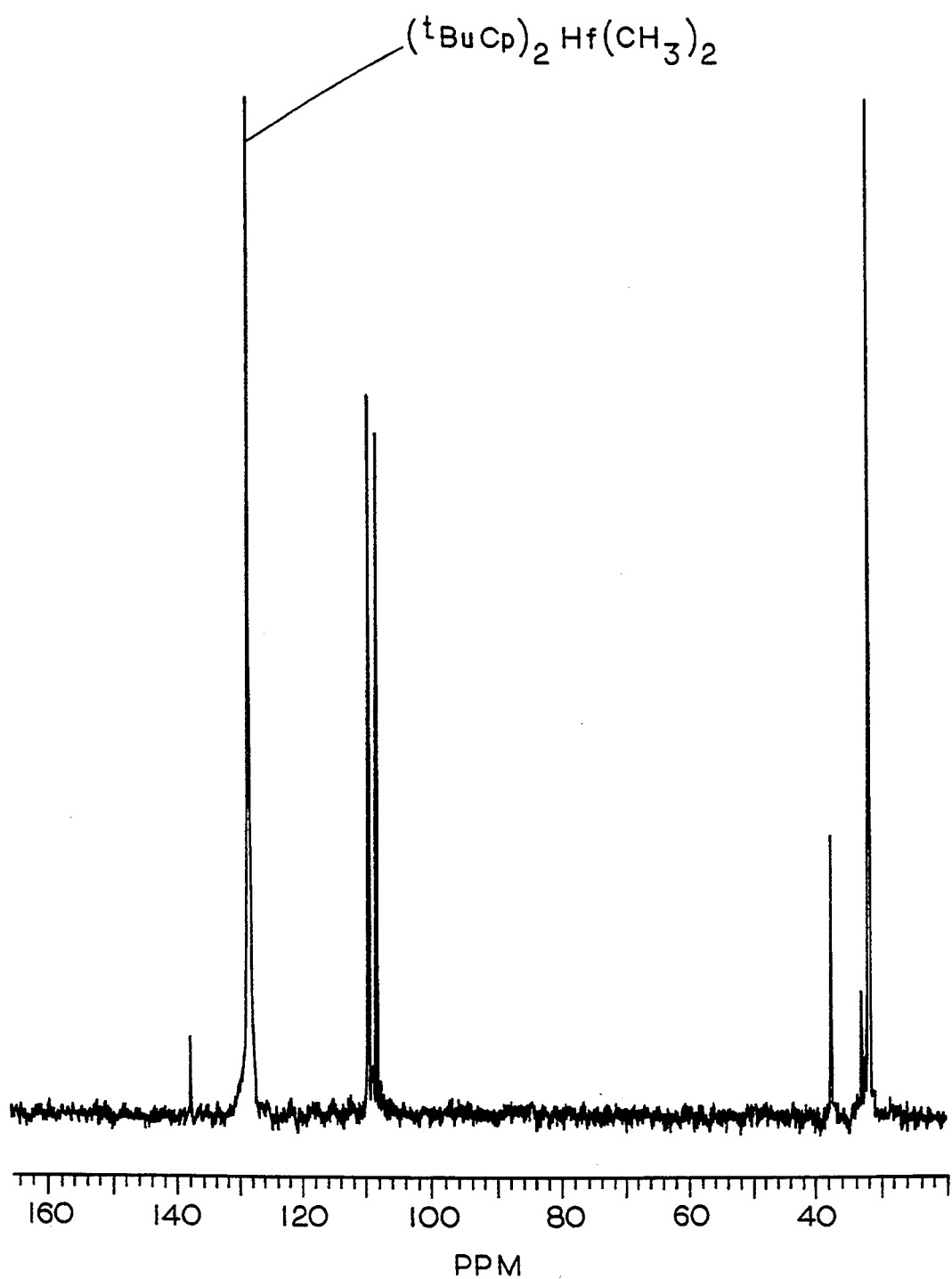
FIG. 7 is a $^{13}$C NMR spectrum of bis(t-butylcyclopentadienyl)hafnium dimethyl [hereafter ($^t$Bu-Cp)$_2$HfMe$_2$].
Figure 8:
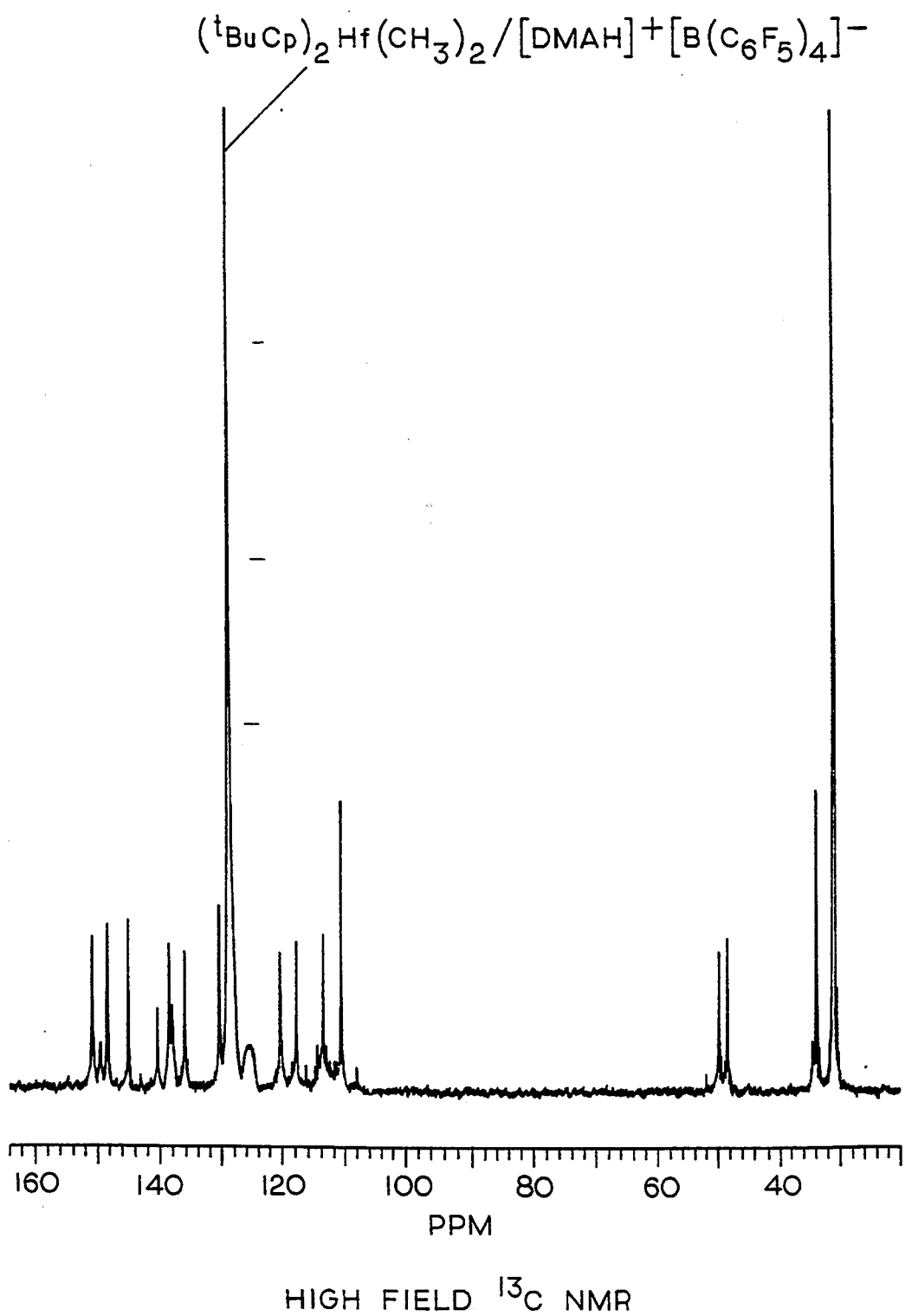
FIG. 8 is a $^{13}$C NMR spectrum of a catalyst prepared by reacting ($^t$Bu-Cp)$_2$HfMe$_2$ with one equivalent of [HDMA][B(pfp)$_4$].

The Lewis base, L', released during catalyst activation plays an important role in determining the stability and structure of the hafnium catalyst. The three coordinate cation [Cp$_2$HfMe]$^+$ thermally decomposes to give several cationic products unless there is a Lewis base present that is capable of coordinating to the cationic center. Cp$_2$HfMe$_2$ and PhNMe$_2$ are sufficiently basic to stabilize the metal center and Bu$_3$N is not. From an electronic point of view one would predict that Bu$_3$N would coordinate more strongly to the cationic center than PhNMe$_2$ because PhMe$_2$NH$^+$ is a much stronger Bronsted acid than Bu$_3$NH$^+$ (by a factor of 10$^6$). This observation leads to the conclusion that steric factors play an important role in determining the ability of a Lewis base to coordinate to [Cp$_2$HfMe]$^+$. For this reason substituted hafnocene catalysts prepared using [DMAH][B(pfp)$_4$] were examined to determine how the number and type of substitutions affect DMA's ability to coordinate to the metal center. The $^{13}$C NMR spectrum of ($^t$Bu—Cp)$_2$HfMe$_2$ is shown in FIG. 7. As expected, three Cp-signals were observed in the aromatic region of the spectrum. The low field signal at 138 ppm is assigned to the ring carbon atom bonded to the $^t$Bu-group; the fact that this carbon is not bonded to a proton was confirmed by DEPT NMR spectroscopy. The two signals at 108 and 109 ppm are bonded to protons and are assigned to the two sets of inequivalent carbon atoms of the Cp-ring. The signal at 38 ppm is assigned to the hafnium methyl groups based on known chemical shifts of neutral methyl hafnocene complexes. The large signal at 31 ppm is assigned to the three methyl groups on the $^t$Bu group. The remaining signal at 32.5 ppm is the quaterary carbon on the $^t$Bu group. The $^{13}$C NMR spectrum of the catalyst prepared by reacting ($^t$Bu-Cp)$_2$HfMe$_2$ with one equivalent of [DMAH][B(pfp)$_4$] is shown in FIG. 8. The fact that one set of $^t$Bu signals (e.g. one quartanary carbon at 34 ppm and one $^t$Bu-methyl signal at 31 ppm was observed suggest that the reaction produces one type of hafnium product and that the $^t$Bu-group remains intact (e.g. the $^t$Bu group does not react with the catalyst center to form a metallated species). The sharp signal at 48 ppm is assigned to the methyl group bonded to the cationic metal center. The relatively broad signal at 50 ppm is assigned to the two methyl groups on the coordinated amine, DMA. No evidence for the existence of free DMA (no signal at 40 ppm) was observed. The fact that the coordinated signal for the DMA methyl groups at 40 ppm is broader than normal suggests the presence of a fluxional or dynamic process which is operating near the NMR time scale. The NMR data are consistent with a structure shown below in Structure XII. Five independent Cp-carbon signals should be observed in the NMR spectrum to be consistent with this structure because the asymmetry caused by coordination of the aniline ligand destroys the plane of symmetry through the $^t$Bu carbon of the Cp-ligands.

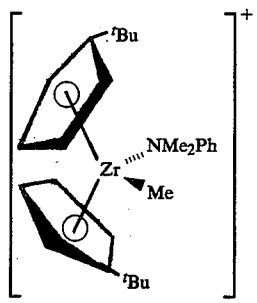

XII.

Figure 9:
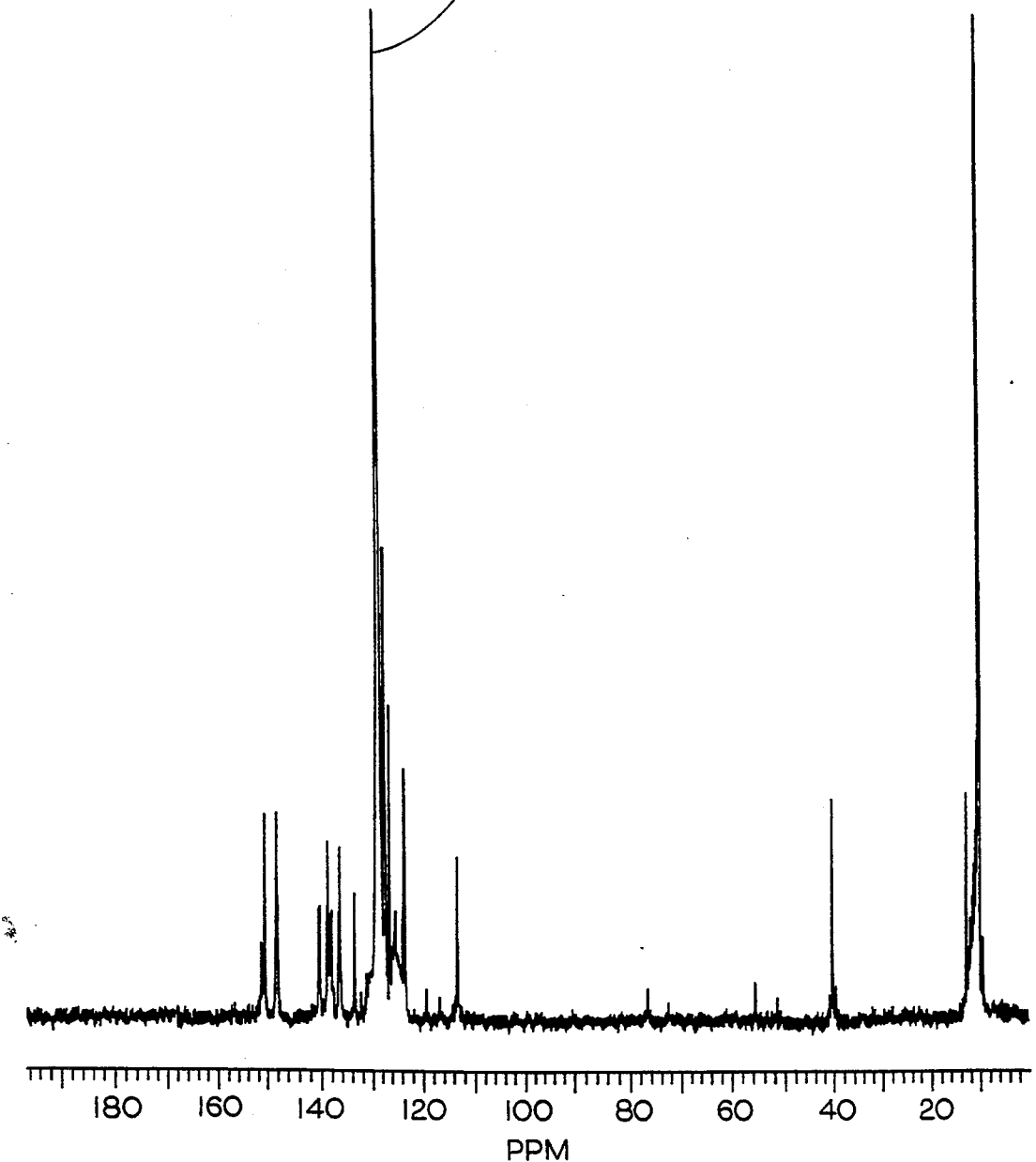
FIG. 9 is an $^{13}$C NMR spectrum of a composition formed after 20 minutes of reacting bis(pentamethylcyclopentadienyl)hafnium dimethyl (hereafter (C$_5$Me$_5$)$_2$HfMe$_2$) with one equivalent of [HDMA][(B(pfp)$_4$)].
Figure 10:
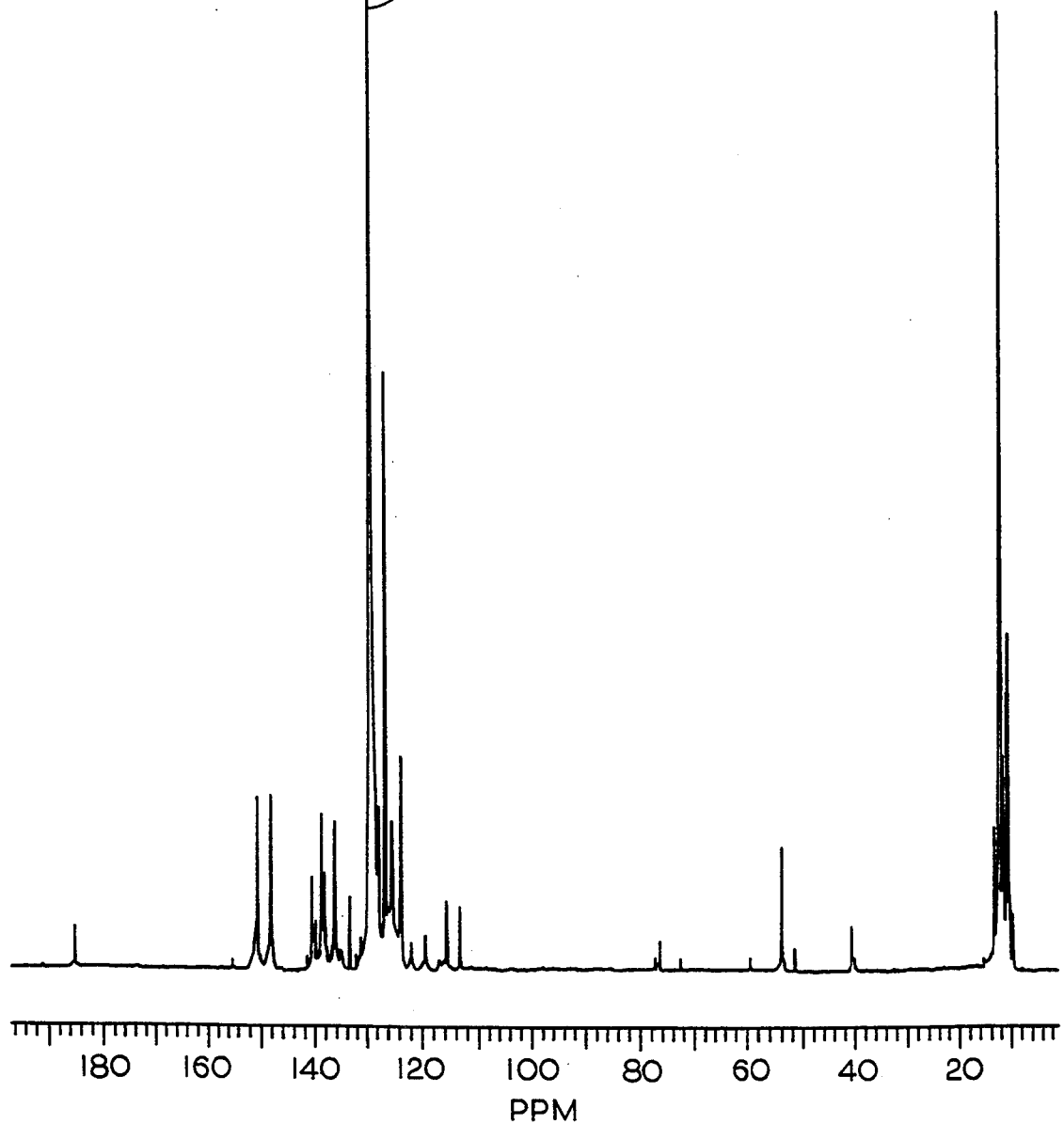
FIG. 10 is an $^{13}$C NMR spectrum of the composition of FIG. 9 taken 20 hours after beginning the reaction.

The NMR spectra of the reaction of bis(pentamethylcyclopentadienyl)zirconium dimethyl (Cp*ZrMe$_2$ where Cp*=C$_5$Me$_5$) with one equivalent of [DMAH][B(pfp)$_4$] after 20 minutes and 20 hours at room temperature are shown in FIG. 9 and 10 respectively. The initial reaction product is unstable and decomposes into several cationic complexes. The signals between 10 and 20 ppm are assigned to the methyl groups attached to Cp* ligands; the fact that there are at least 6 different singlets in this region suggests that there are several chemically distinct metallocene complexes in solution. The presence of free DMA is observed at 20 minutes (the methyl groups of free DMA appear at 40 ppm).

The bulk imposed by the Cp* ligands prevents coordination of the DMA and the naked cation, [Cp*$_2$HfMe][B(pfp)$_4$], is thermally unstable and quickly decomposes by loss of methane to give various metallated products. The ionic decomposition products (or at least some of them) are active olefin polymerization catalysts. The structure and thermal stability of Cp$_2$ZrMe$^+$ catalysts derived from [DMAH][B(pfp)$_4$] and [Bu$_3$NH][B(pfp)$_4$] were compared with the analogous hafnium systems discussed earlier.

Figure 11:
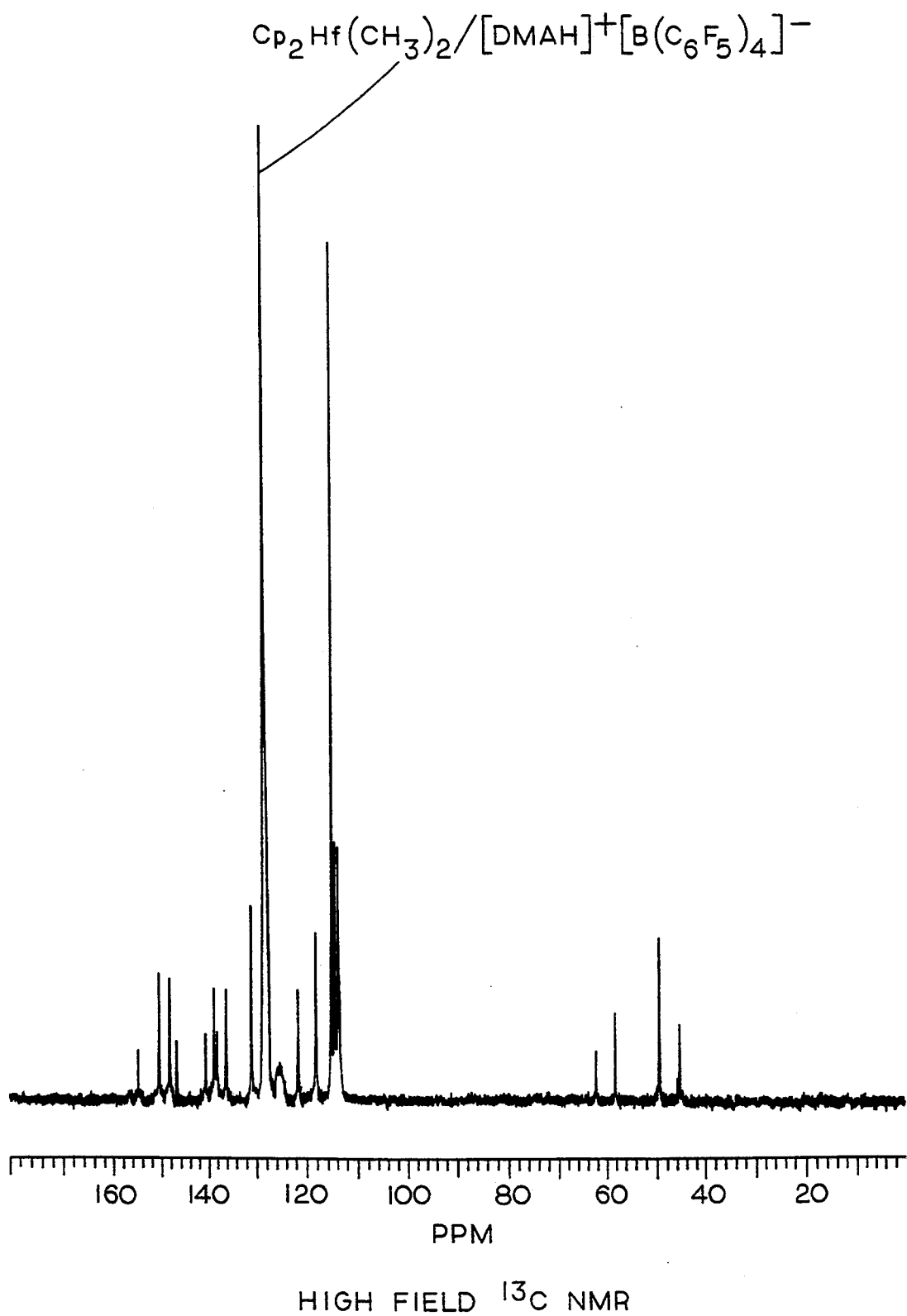
FIG. 11 is a $^{13}$C NMR spectrum of the product resulting from the reaction of bis(cyclopentadienyl)zirconium dimethyl [hereafter Cp$_2$ZrMe$_2$] with [HDMA][B(pfp)$_4$] collected 20 minutes after the beginning of reaction.
Figure 12:
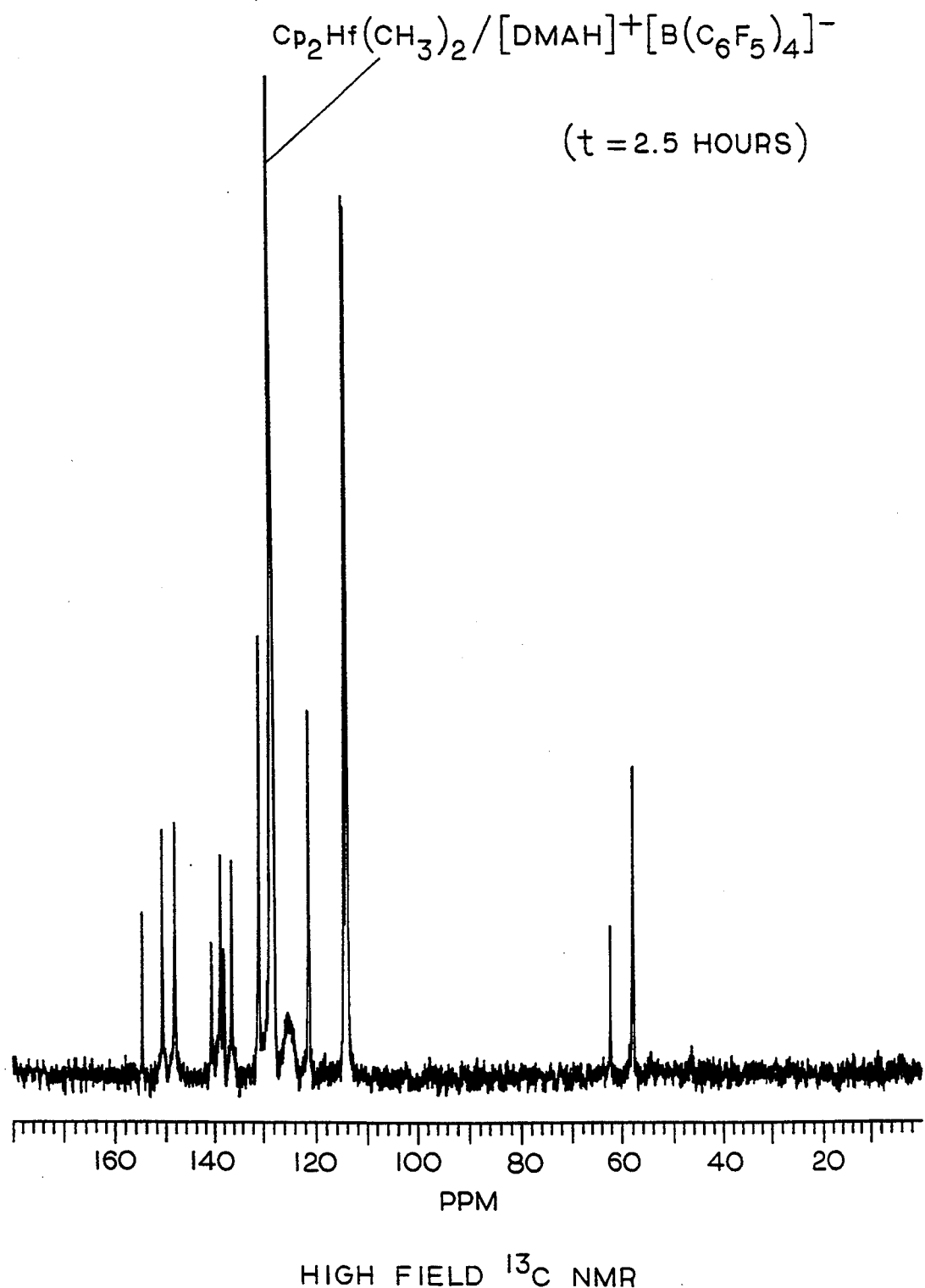
FIG. 12 is a $^{13}$C NMR spectrum of the product resulting from the reaction of FIG. 11 collected at 2.5 hours after the beginning of the reaction.

The $^{13}$C NMR spectra of the reaction of Cp$_2$ZrMe$_2$ with one equivalent of [DMAH][B(pfp)$_4$] collected at t=10 minutes and t=2.5 hours are shown in FIGS. 11 and 12. After 10 minutes signals due to [Cp$_2$ZrMe(DMA)][B(pfp)$_4$] were observed along with a new complex having two Cp-signals of equal intensity and high field signals at 62 ppm and 58 ppm. After 2.5 hours (12) all of the original methyl cation, [Cp$_2$ZrMe(DMA)][B(pfp)$_4$], had decomposed giving a high yield of the complex giving two equal intensity Cp signals. Proton coupled $^{13}$C NMR spectroscopy indicates that the signal at 62 ppm is a methylene group (—CH$_2$—) and the signal located at 58 ppm is a methyl group (—CH$_3$—). These are consistent with the structure shown below in Structure XIII.

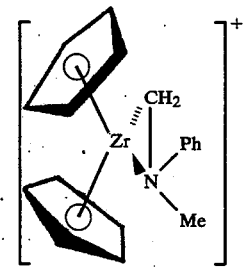

XIII.

The metallated complex produced by decomposition of the methyl cation (Figure XIV) is an active olefin polymerization catalyst capable of producing a polymer chain having an N-methylaniline head group.

There are differences between the properties of [Cp$_2$ZrMe(DMA)][B(pfp)$_4$] and [Cp$_2$HfMe(DMA)][B(pfp)$_4$]. First, the thermal stability of [Cp$_2$ZrMe(DMA)][B(pfp)$_4$] is much less than the hafnium derivative. The half life of the hafnium catalyst is 18 hours compared to 1 hour for the zirconium derivative. Second, the thermal decomposition of the zirconium complex produces one well characterized cationic product while the hafnium catalyst produces several products. It should be noted that decomposition of [Cp$_2$ZrMe(DMA)][B(pfp)$_4$] to give the metallated product is a possible chain transfer reaction (when Zr—Me is Zr-polymer). The fact that this reaction occurs much more rapidly correlates with the observation that the zirconium catalyst produces lower molecular weight products (i.e. less stable chains yields more rapid chain transfer). The larger decomposition, and chain transfer rates observed for zirconium catalysts relative to hafnium systems reflects the fact that the metal-carbon bond (M-Me or M-polymer) in the zirconium complexes is significantly weaker than in the corresponding hafnium systems.

Figure 13:
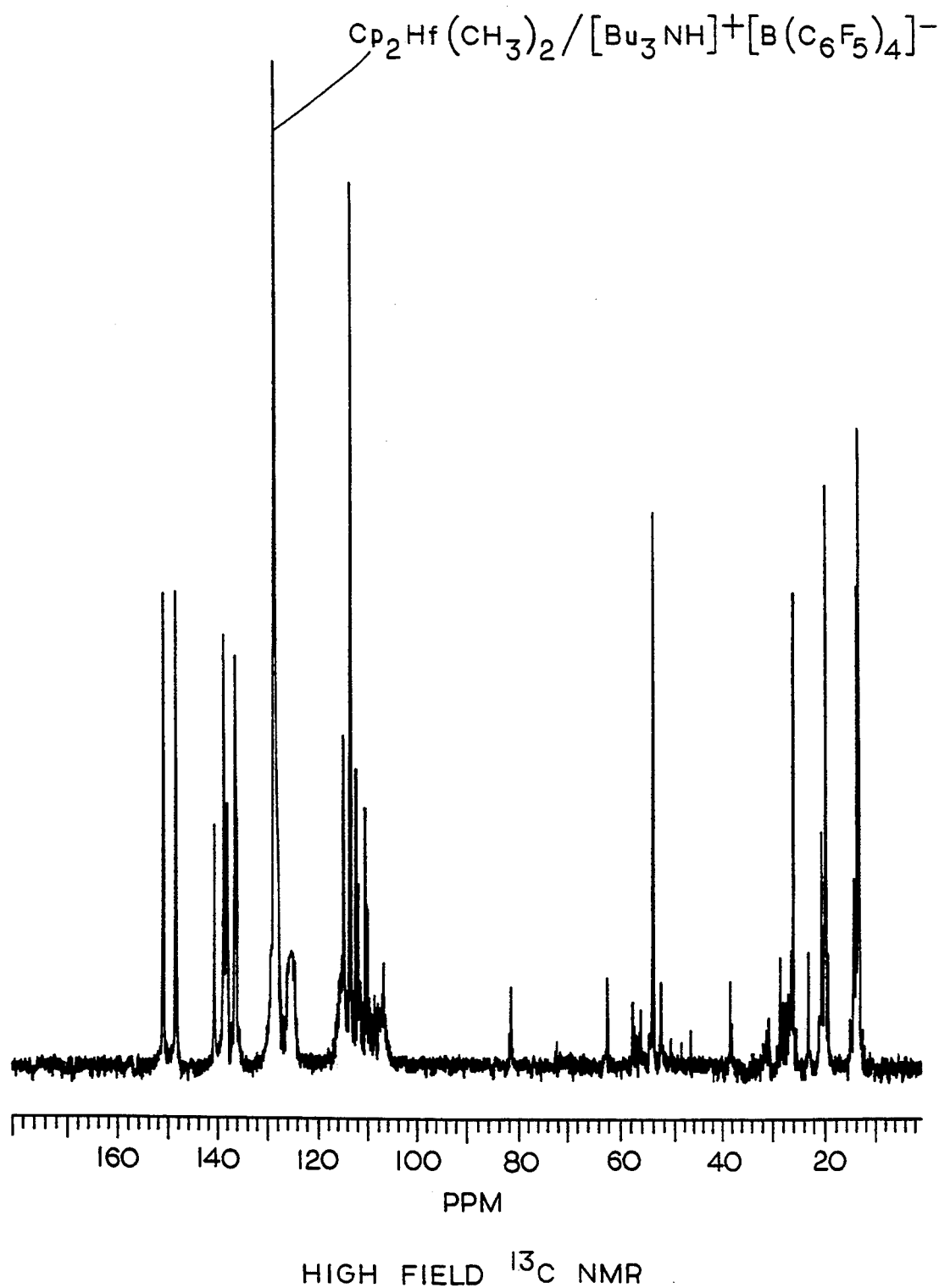
FIG. 13 is a $^{13}$C NMR spectrum of the produce resulting from the reaction of Cp$_2$ZrMe$_2$ with tributylammonium tetra(pentafluorophenyl)boron (hereafter [Bu$_3$NH][B(pfp)$_4$]) collected 20 minutes after reaction.
Figure 14:
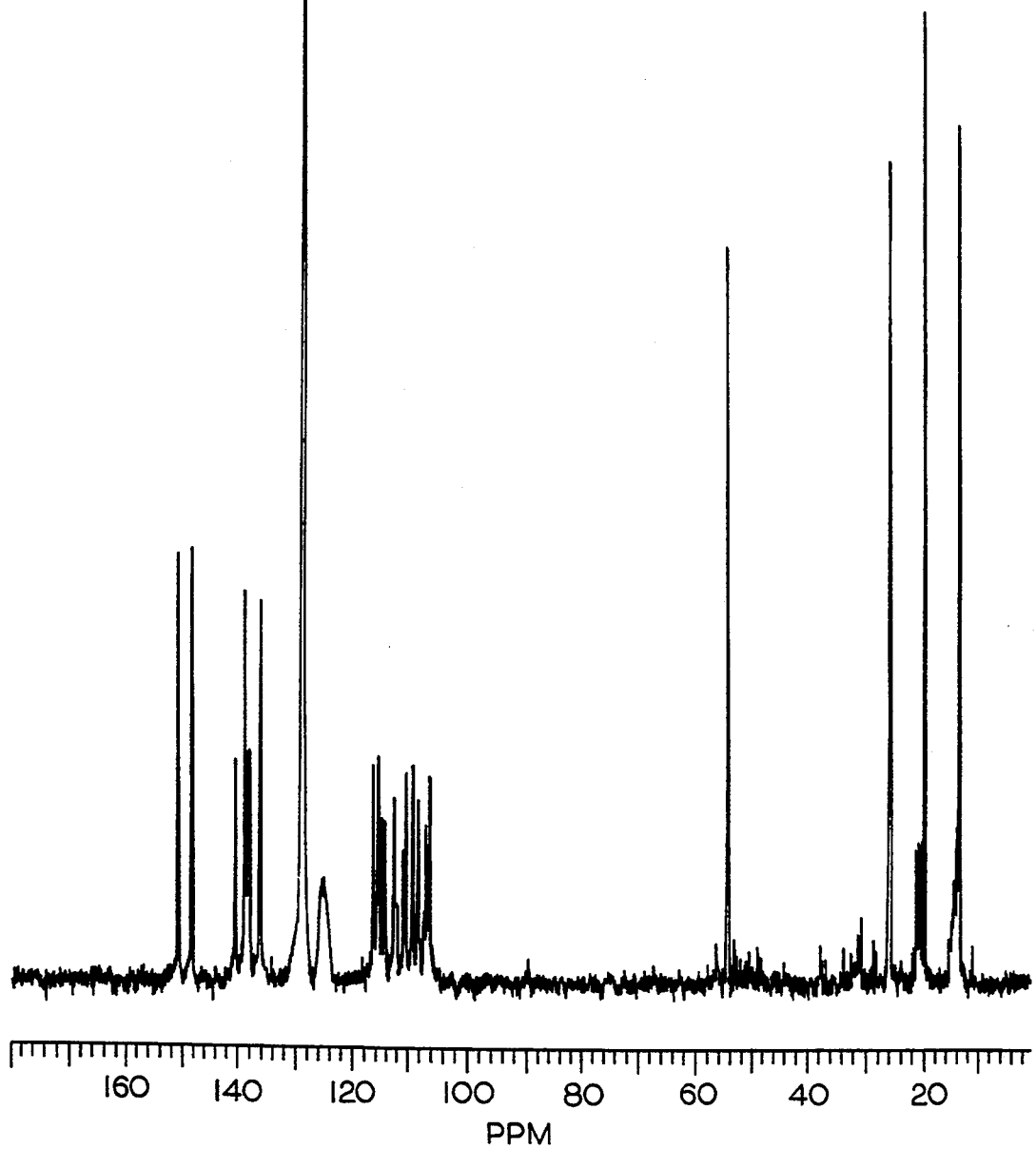
FIG. 14 is a $^{13}$C NMR spectrum of the product of FIG. 13 collected 20 hours after reaction.

The $^{13}$C NMR spectra of the reaction of Cp$_2$ZrMe$_2$ with [Bu$_3$NH][B(pfp)$_4$] at T=20 minutes and T=20 hours are shown in FIGS. 13 and 14 respectively. The presence of free amine and many unidentified cationic products are again observed. Again, Bu$_3$N is too bulky to coordinate to the metallocene center and the resulting three coordinate cation is thermally unstable.

In the preferred method of preparing the catalyst compostions of the present invention a bis(cyclopentadienyl) metal compound, said metal being selected from the Group consisting of titanium, zirconium, and hafnium, said compound containing two, independently, substituted or unsubstituted cyclopentadienyl radicals and one or two lower alkyl substituents and/or one or two hydride substituents will be combined with a trisubstituted ammonium salt of a fluorinated non-coordinating anion such as [B(C$_6$F$_5$)$_4$]$^-$ or [B(C$_6$F$_5$)$_3$Q]$^-$ (where Q is an monoanionic non-bridging radical coordinated to boron as defined earlier). Each of the trisubstitutions of the ammonium cation will be the same or a different lower alkyl or aryl radical. By lower alkyl is meant an alkyl radical containing from one to four carbon atoms. Tri(n-butyl) ammonium tetra(pentafluorophenyl)boron and N,N-dimethylanilinium tetra(pentafluorophenyl)boron are particularly preferred activator compounds.

In a most preferred embodiment of the present invention, bis(cyclopentadienyl)zirconium dimethyl or bis(cyclopentadienyl)hafnium dimethyl will be reacted with N,N-dimethylanilinium tetra(pentafluorophenyl)boron to produce the most preferred catalyst of the present invention. The two components will be combined at a temperature within the range from about 0° C. to about 100° C. The components will be combined, preferably, in an aromatic hydrocarbon solvent, most preferably toluene. Nominal holding times within the range from about 10 seconds to about 60 minutes will be sufficient to produce both the preferred and most preferred catalyst of this invention.

In some cases, the stable catalyst formed by the method of this invention may be separated from the solvent and stored for subsequent use. Less stable catalyst, however, will, generally, be retained in solution until ultimately used in the polymerization of olefins, diolefins and/or acetylenically unsaturated monomers. Alternatively, any of the catalysts prepared by the method of this invention may be retained in solution for subsequent use or used directly after preparation as a polymerization catalyst. Moreover, and as indicated supra, the catalyst may be prepared in situ during a polymerization reaction by passing the separate components into the polymerization vessel where the components will contact and react to produce the improved catalyst of this invention.

In a preferred embodiment, the catalyst, immediately after formation, will then be used to polymerize a lower α-olefin particularly ethylene or propylene, most preferably ethylene, at a temperature within the range from about 0° C. to about 100° C. and at a pressure within the range from about 15 to about 500 psig. In a most preferred embodiment of the present invention, the most preferred catalyst will be used either to homopolymerize ethylene or to copolymerize ethylene with a lower α-olefin having from 3 to 6 carbon atoms, thereby yielding a plastic or an elastomeric copolymer. In both the preferred and most preferred embodiments, the monomers will be maintained at polymerization conditions for a nominal holding time within the range from about 1 to about 60 minutes and the catalyst will be used at a concentration within the range from about 10$^{-5}$ to about 10$^{-1}$ moles per liter of solvent.

Having thus broadly described the present invention and a preferred and most preferred embodiment thereof, it is believed that the same will become even more apparent by reference to the following examples. It will be appreciated, however, that the examples are presented solely for purposes of illustration and should not be construed as limiting the invention. All of the examples were completed either under an argon blanket by standard Schlenk techniques or under a helium blanket in a Vacuum Atmospheres HE43-2 drybox. The solvents used in the experiments were rigorously dried under nitrogen by standard techniques. The boron and metallocene reagents used in the examples were either purchased or prepared following published techniques. The zwitterionic complexes (Examples 1, 4, 10 and 22) were characterized by solid state $^{13}$C NMR spectroscopy and solution $^1$H NMR spectroscopy. The tetra(p-ethylphenyl)boron zwitterionic derivative isolated in Example 10 was further characterized by single crystal x-ray crystallography.

EXAMPLE 1

In this example, a stable, isolable polymerization catalyst was prepared by combining 0.65 g of tri(n-butyl)ammonium tetra(phenyl)boron with 0.50 g of bis(pentamethylcyclopentadienyl)zirconium dimethyl. The combination was accomplished by first suspending the tri(n-butyl)ammonium tetra(phenyl)boron in 50 ml of toluene and then adding the bis(pentamethylcyclopentadienyl)zirconium dimethyl. The combination was accomplished at room temperature and contacting between the two compounds was continued for 1 hour. After 1 hour, an insoluble orange precipitate separated from solution leaving a clear mother liquor. The orange precipitate was isolated by filtration, washed three times with 20 ml of pentane and dried in vacuo. 0.75 g of the orange precipitate was recovered. A portion of this product was analyzed and it was found to contain a single organometallic compound having the following general formula:

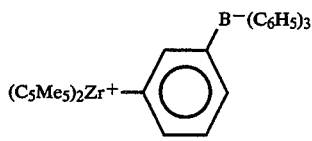

wherein Me is a methyl radical

EXAMPLE 2

In this example, ethylene was polymerized by adding 0.05 g of the orange precipitate recovered in Example 1 to 20 ml of toluene at room temperature in a 100 ml side armed flask and then adding excess ethylene at atmospheric pressure while maintaining vigorous agitation. An immediate exotherm was detected and the formation of polyethylene observed as the addition of ethylene continued.

EXAMPLE 3

In this example, ethylene was polymerized by first suspending 0.05 g of the orange precipitate prepared in Example 1 to 20 ml of chlorobenzene in a 100 ml side armed flask and then adding excess ethylene at atmospheric pressure while maintaining agitation. An immediate exotherm was detected and the formation of polyethylene was observed as the addition of ethylene continued.

EXAMPLE 4

In this example, an active, isolable olefin polymerization catalyst was prepared by first suspending 0.75 g of tri(n-butyl)ammonium tetra(p-tolyl)boron in 50 ml of toluene and then adding 0.52 g of bis(pentamethylcyclopentadienyl)zirconium dimethyl. The mixture was stirred at room temperature for 1 hour. After 1 hour, an insoluble orange precipitate separated from solution. The orange precipitate was isolated by filtration, washed three times with 20 ml of pentane and dried in vacuo. 0.55 g of the orange precipitate were recovered. The orange precipitate was analyzed and found to contain an organometallic compound having the following structure:

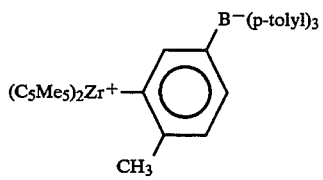

wherein Me is a methyl radical.

EXAMPLE 5

In this example, ethylene was polymerized at atmospheric pressure by passing ethylene into a 20 ml sample of crude reaction mixture from Example 4 in a 100 ml side armed flask. The ethylene was rapidly polymerized.

EXAMPLE 6

In this example, ethylene was polymerized at 40 psig by dissolving 0.02 g of the orange precipitate produced in Example 4 in 100 ml of toluene in a Fisher-Porter glass pressure vessel, heating the solution to 80C. and then passing ethylene into said solution at 40 psig for 20 minutes. 2.2 g of polyethylene were obtained and the average molecular weight of the polymer was 57,000. The polymer had a polydispersity of 2.5.

EXAMPLE 7

In this example, ethylene and acetylene were copolymerized by dissolving 0.05 g of the orange precipitate from Example 4 in toluene and then adding 2 ml of purified acetylene at atmospheric pressure in an NMR Lube. An immediate color change from orange to yellow was noted. After five minutes, 5 ml of ethylene at atmospheric pressure were added to this mixture and an immediate exotherm was observed as was polymer formation.

EXAMPLE 8

In this example, an active isolable olefin polymerization catalyst was produced by first suspending 0.56 g of tri(n-butyl)ammonium tetra(o-tolyl)boron in 50 mil of toluene and then adding 0.25 g of bis(cyclopentadienyl)zirconium dimethyl. The mixture was stirred at room temperature for 1 hour. After 1 hour an insoluble yellow precipitate separated from an orange solution. The yellow precipitate was isolated by filtration, washed three times with 20 ml of pentane and dried in vacuo. 0.26 g of the yellow precipitate were recovered.

EXAMPLE 9

In this example, excess ethylene was added at atmospheric pressure to a portion of the orange mother liquor from Example 8 in a 100 ml side armed flask and polyethylene formed. Ethylene was also contacted with a portion of the yellow precipitate, which precipitate was suspended in toluene in a 50 ml side armed flask and again polyethylene was formed.

EXAMPLE 10

In this example, an active, isolable olefin polymerization catalyst was produced by first suspending 1.20 g of tri(n-butyl)ammonium tetra(p-ethylphenyl) boron in 50 ml of toluene and then adding 0.76 g of bis(pentamethylcyclopentadienyl)zirconium dimethyl. The mixture was stirred at room temperature for 1 hour. After 1 hour, the reaction mixture was evaporated to dryness. The crude orange solid, which was produced, was recrystallized from hot toluene to give 1.0 g of orange-red crystals. A portion of this product was analyzed and confirmed to be an organometallic compound having the following structure:

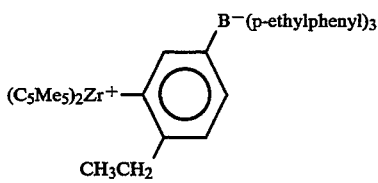

wherein Me is a methyl radical.

EXAMPLE 11

In this example, ethylene was polymerized by dissolving 0.10 g of the orange-red crystals from Example 10 in toluene and then placing the solution in a steel autoclave under nitrogen pressure. Ethylene at 100 psig was then introduced into the autoclave and the autoclave heated to 80C. with agitation. After 10 minutes, the reactor was vented to atmospheric pressure and opened. The yield of linear polyethylene was 27 g having a weight average molecular weight of about 52,000.

EXAMPLE 12

In this example, an active, isolable olefin polymerization catalyst was prepared by first suspending 0.78 g of tri(n-butyl)ammonium tetra(m,m-dimethylphenyl)boron in 50 ml of toluene and then adding 0.50 g of bis(pentamethylyclopentadienyl)zirconium dimethyl. The mixture was stirred at room temperature for 1 hour. After 1 hour, the reaction mixture was evaporated to dryness. The resulting crude red-brown solid was washed with 30 ml of pentane and dried in vacuo to yield 0.56 g of a toluene soluble brown solid. Both the brown solid and the crude reaction mixture were dissolved in 40 ml of toluene in a 100 ml side armed flask and were observed to polymerize ethylene at atmospheric pressure.

EXAMPLE 13

In this example, two active, isolable olefin polymerization catalysts were prepared by first dissolving 0.78 g of tri(n-butyl)ammonium tetra(o,p-dimethylphenyl)boron in 30 ml of toluene and 15 ml of pentane. The solution was then cooled to −30C. and 0.50 g of bis(pentamethylcyclopentadienyl)zirconium dimethyl were added. The mixture was warmed to room temperature with agitation and held for 4 hours. A yellow precipitate was separated from a purple reaction mixture by filtration. The yellow precipitate was dried in-vacuo to give 0.62 g of product. After separation of the yellow precipitate, the purple mother liquor was evaporated to dryness to give 0.32 g of a purple glassy solid. The yellow and purple products polymerized ethylene in deutero-toluene in NMR tubes.

EXAMPLE 14

In this example, an olefin polymerization catalyst was prepared by combining 0.06 g of bis(1,3-bis(trimethylsilyl)cyclopentadienyl)zirconium dimethyl, 0.05 g of N,N-diethylanilinium tetra(phenyl)boron and 1 ml of deuterobenzene in an NMR tube and allowing the components to react. The NMR spectrum showed complete loss of starting materials after 20 minutes at room temperature. The reaction mixture was then divided into two portions, diluted with 20 ml toluene, and placed in 50 ml side armed flasks. Ethylene was added to one portion and propylene to the other. Rapid polymerization was observed in both cases.

EXAMPLE 15

In this example, an active olefin polymerization catalyst was prepared by first suspending 0.87 g of tri(n-butyl)ammonium tetra(p-tolyl)boron in 50 ml of toluene and then adding 0.50 g of (pentamethylcyclopentadienyl)(cyclopentadienyl)zirconium dimethyl. The reaction was stirred at room temperature for 18 hours to give a blue-green homogenous solution. The reaction mixture was dried in-vacuo, washed with 30 ml of pentane, and then redissolved in 100 ml of toluene. The resulting blue-green solution was filtered into a glass pressure vessel and stirred under 1.5 atmospheres of ethylene. An immediate exotherm and polymer formation was observed upon exposure of ethylene. The yield of polyethylene was 4.5 g after 15 minutes.

EXAMPLE 16

In this example, an olefin polymerization catalyst was prepared by first suspending 0.1 g of tri(n-butyl)ammonium tetra(p-ethylphenyl)boron in 5 ml of $d_6$-benzene and then adding 0.05 g of (pentamethylcyclopentadienyl) (cyclopentadienyl)zirconium dimethyl. The reaction was complete after 30 minutes. The green solution was then dried in-vacuo to give a green glassy solid. The crude green product was extracted with 20 ml of toluene. In separate experiments, the toluene extract was exposed to ethylene, to propylene and to a mixture of ethylene and propylene. In each case significant polymerization activity was observed.

EXAMPLE 17

In this example, an active olefin polymerization catalyst was prepared by first suspending 0.22 g of tri(n-butyl)ammonium tetra(pentafluorophenyl)boron in 50 ml of toluene and then adding 0.10 g of bis(pentamethylcyclopentadienyl) zirconium dimethyl. The reaction vessel was capped with a rubber septum and stirred at room temperature. After 10 minutes the reaction mixture (now yellow and homogeneous) was pressurized with 1.5 atmospheres of ethylene and stirred vigorously. Rapid polymerization of ethylene was observed causing a significant increase in the reaction temperature (from room temperature to at least 80C.) during the first 5 minutes of polymerization. After 15 minutes, the reaction vessel was vented and methanol was added to kill the still active catalyst. The yield of linear polyethylene was 3.7 g.

EXAMPLE 18

In this example, an active olefin polymerization catalyst was prepared by suspending 0.34 g of tri(n-butyl)ammonium tetra(pentafluorophenyl)boron in 50 ml of toluene and then adding 0.13 g of (pentamethylcyclopentadienyl)(cyclopentadienyl)zirconium dimethyl. The reaction vessel was capped with a rubber septum and stirred at room temperature. After 10 minutes the reaction mixture (a yellow solution above an insoluble orange oil) was pressurized with 1.5 atmospheres of ethylene and stirred vigorously. Rapid polymerization of ethylene was observed causing a significant increase in the reaction temperature (from room temperature to at least 80C.) during the first minutes of polymerization. After 10 minutes, the reaction vessel was vented and methanol was added to kill the still active catalyst. The yield of linear polyethylene was 3.7 g.

EXAMPLE 19

In this example, an active olefin polymerization catalyst was prepared by combining 0.18 g of tri(n-butyl) ammonium tetra(pentafluorophenyl)boron in 50 ml of toluene and then adding 0.12 g of bis [1,3-bis(trimethylsilyl)cyclopentadienyl]zirconium dimethyl. The reaction vessel was capped with a rubber septum and stirred at room temperature. After 10 minutes the reaction mixture (a yellow solution above an insoluble yellow oil) was pressurized with 1.5 atmospheres of ethylene and stirred vigorously. Rapid polymerization of ethylene was observed causing a significant increase in the reaction temperature (from room temperature to at least 80C.) during the first minutes of polymerization. After 10 minutes the reaction vessel was vented and methanol was added to kill the still active catalyst. The yield of linear polyethylene was 2.1 g.

EXAMPLE 20

In this example, an active olefin polymerization catalyst was prepared by suspending 0.34 g of tri(n-butyl)ammonium tetra(pentafluorophenyl)boron in 50 ml of toluene and then adding 0.10 g of bis(cyclopentadienyl)zirconium dimethyl. The reaction vessel was capped with a rubber septum and stirred at room temperature. After 10 minutes the reaction mixture (a yellow solution above an insoluble orange oil) was pressurized with 1.5 atmospheres of ethylene and stirred vigorously. Rapid polymerization of ethylene was observed causing a significant increase in the reaction temperature (from room temperature to at least 80C.) during the first minutes of polymerization. After 10 minutes the reaction vessel was vented and methanol was added to deactivate the still active catalyst. The yield of linear polyethylene was 3.7 g.

EXAMPLE 21

In this example, an active olefin polymerization catalyst was prepared by combining 0.12 g of tri(n-butyl)ammonion tetra(pentafluorophenyl)boron and 0.04 g of bis(cyclopentadienyl)zirconium dimethyl in 100 ml of toluene in a 250 ml flask. The flask was capped with a rubber septum and stirred at 60C. for 3 minutes. Ethylene 1.5 atmospheres and 3 mi of 1-hexene were then added to the flask. After 20 minutes, the flask was vented and methanol was added to deactivate the still active catalyst. The white polymeric product was collected by filtration and dried in vacuo to yield 8.0 g of a hexane-ethylene copolymer. The melting point of the copolymer was 125C.

EXAMPLE 22

In this example, an active, isolable olefin polymerization catalyst was prepared by first suspending 1.30 g of tri(n-butyl)ammonium tetra(p-tolyl) boron in 50 of toluene and then adding 1.00 g of bis(ethyltetramethylcyclopentadienyl)zirconium dimethyl. The mixture was stirred at room temperature for 1 hour. After 1 hour, an insoluble orange precipitate separated from solution. The orange precipitate was isolated by filtration, washed three times with 20 ml of pentane and dried in vacuo. 0.55 g of the orange precipitate were recovered. The orange precipitate was analyzed and found to contain an organometallic compound having the following structure:

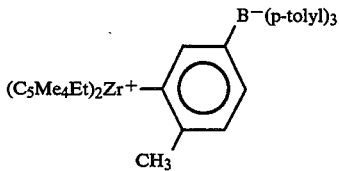

wherein Et is an ethyl radical and Me is a methyl radical.

EXAMPLE 23

In this example, 0.05 g of the orange precipitate produced in Example 22 was dissolved in 2 ml of deuterotoluene and placed in a 5 mm NMR tube and capped with a rubber septum. Ethylene (2 ml at 1 atm) was added via syringe and immediately polymerized.

EXAMPLE 24

In this example, ethylene and 1-butene were copolymerized in a hexane diluent by adding under a nitrogen atmosphere to a 1 L stainless-steel autoclave, previously flushed with nitrogen and containing 400 ml of dry oxygen-free hexane, 40 ml of a toluene solution containing 4 mg of bis(cyclopentadienyl)zirconium dimethyl and 12 mg of tri(n-butyl)ammonium tetra(pentafluorophenyl)boron. 1-butene (200 ml) was added to the autoclave, which was further pressurized with 65 psig of ethylene. The autoclave was stirred and heated for 7 minutes at 60C. The reactor was vented and cooled and the contents dried. The yield of copolymer isolated was 9.2 g. The weight-average molecular weight of the polymer was 108,000 and the molecular weight distribution was 1.97. A compositional distribution analysis indicated a breadth index of 88%.

EXAMPLE 25

In this example, ethylene and 1-butene were copolymerized in a hexane diluent by adding under a nitrogen atmosphere to a 1 L stainless-steel autoclave, previously flushed with nitrogen and containing 400 ml of dry, oxygen-free hexane, 40 ml of a toluene solution containing 4 mg of bis(cyclopentadienyl)zirconium dimethyl and 12 mg of tri(n-butyl)ammonium tetra(pentafluorophenyl)boron. 1-butene (200 ml) was added to the autoclave, which was further pressurized with 65 psig of ethylene. The autoclave was stirred and heated at 50C. for 10 minutes. The autoclave was vented and cooled and the contents dried. The yield of copolymer isolated was 7.1 g. The weight-average molecular weight of the polymer was 92,000 with a molecular weight distribution of 1.88. Analysis by $^{13}$C NMR spectroscopy indicated a reactivity ratio $(r_1r_2)$ of 0.145.

EXAMPLE 26

In this example, ethylene and 1-butene were copolymerized in a hexane diluent by adding under a nitrogen atmosphere to a 1 L stainless-steel autoclave, previously flushed with nitrogen and containing 400 ml of dry, oxygen-free hexane, 25 ml of a toluene solution containing 9 mg of bis[(t-butyl)cyclopentadienylzirconium dimethyl and 2.9 mg of N,N-dimethylanilinium tetra(pentafluorophenyl)boron. 1-butene (100 ml) was added to the autoclave, which was further pressurized with 65 psig of ethylene. The autoclave was stirred and heated at 50C. for 1 hour. The autoclave was vented and cooled and the contents dried. The yield of copolymer isolated was 27.2 g. The weight-average molecular weight of the polymer was 23,000 with a molecular weight distribution of 1.8. Analysis of the composition distribution indicated a median comonomer content of 6.3 mole % and a breadth index of 81%.

EXAMPLE 27

In this example, a stirred 100 ml steel autoclave reaction vessel which was equipped to perform Ziegler-Natta polymerization reactions at pressures up to 2500 bar and temperatures up to 300C. was used. The temperature of the cleaned reactor containing ethylene at low pressure was equilibrated at the desired reaction temperature of 160C. The catalyst solution was prepared by dissolving 259 mg of a zwitterionic catalyst (prepared from bis(ethyltetramethylcyclopentadienyl)zirconium dimethyl and tri(n-butyl)ammonium tetra(p-ethylphenyl) boron in 10.0 ml of distilled toluene under nitrogen. A 0.4 ml portion of this catalyst solution was transferred by low-pressure nitrogen into a constant-volume injection tube, which was held at 25C. Ethylene was pressured into the autoclave at a total pressure of 1500 bar. The reactor contents were stirred at 1000 rpm for 1 minute at which time the catalyst solution was rapidly injected into the stirring reactor with excess pressure. The temperature and pressure changes were recorded continuously for 120 seconds at which time the contents were rapidly vented, yielding the polymer. The reactor was washed with xylene to collect any polymer remaining inside and all polymer was dried in vacuo. The yield of polyethylene isolated was 0.56 g. This polymer had a weight-average molecular weight of 21,900, a molecular weight distribution of 10.6 and a density of 0.965 g/ml.

EXAMPLE 28

In this example, ethylene was polymerized by adding under a nitrogen atmosphere to a 1 L stainless-steel autoclave, previously purged with nitrogen and containing 400 ml of dry, oxygen-free hexane, first a solution of 15 mg of bis(cyclopentadienyl)hafnium dimethyl in 30 ml of toluene, then, after 5 minutes, a toluene solution (50 ml) containing 12 mg of bis(cyclopentadienyl)hafnium dimethyl and 30 mg of tri(n-butyl)ammonium tetrakis(perfluorophenyl)boron. The autoclave was pressured with 90 psig of ethylene and stirred at 60C. After 1 hour, the autoclave was vented and opened. The yield of linear polyethylene isolated was 73.8 g. This material had a weight-average molecular weight of 1,100,000 and a molecular weight distribution of 1.78.

EXAMPLE 29

In this example, ethylene and propylene were copolymerized in a hexane diluent by adding under a nitrogen atmosphere to a 1 L stainleess-steel autoclave previously flushed with nitrogen and containing 400 ml of dry, oxygen-free hexane, first a solution of 15 mg bis(cyclopentadienyl)hafnium dimethyl in 25 ml of toluene, stirring for 5 minutes, then 50 ml of a toluene solution containing 17 mg bis(cyclopentadienyl)hafnium dimethyl and 42 mg of tri(n-butyl)ammonium tetra(pentafluorophenyl)boron. Propylene (200 ml) was added to the autoclave, which was further pressured with an additional 50 psig of ethylene. The autoclave was stirred at 60C. for 15 minutes. The reactor was vented and opened and the residual hexane in the contents evaporated under a stream of air. The yield of copolymer isolated was 61.0 g. This copolymer, which was 35.1 wt % ethylene, had a weight-average molecular weight of 103,000 and a molecular weight distribution of 2.3. Analysis by $^{13}$C NMR spectroscopy indicated a statistically random copolymer.

EXAMPLE 30

In this example, ethylene and propylene were copolymerized in bulk propylene by adding under a nitrogen atmosphere to a 1 L stainless-steel autoclave preeviously flushed with nitrogen 50 ml of a toluene solution containing 36 mg of bis(cyclopentadienyl)hafnium dimethyl and 11 mg of N,N-dimethylanilinium tetra(pentafluorophenyl)boron. Propylene (400 ml) was added to the autoclave, which was further pressurized with 120 psig of ethylene. After stirring for 15 minutes at 50C., the reactor was vented and opened and the contents dried under a stream of air. The yield of copolymer isolated was 52.6 g. The copolymer, which was 38.1 wt % ethylene, had a weight-average molecular weight of 603,000 and a molecular weight distribution of 1.93.

EXAMPLE 31

In this example, ethylene and 1-butene were copolymerized in a hexane diluent by adding under a nitrogen atmosphere to a 1 L stainless-steel autoclave, previously flushed with nitrogen and containing 400 ml of dry, oxygen-free hexane, first a 30 mi of a toluene solution containing 15 mg of bis(cyclopentadienyl hafnium dimethyl, then after stirring for 5 minutes, 30 ml of a toluene solution containing 12 mg of bis(cyclopentadienyl)hafnium dimethyl and 30 mg of tri(n-butyl)ammonium tetra(pentafluorophenyl)boron. 1-butene (50 ml) was added to the autoclave, which was further pressurized with 65 psig of ethylene. The autoclave was stirred and heated to 50C. for 1 hour. The reactor was vented and opened and the contents dried in a vacuum oven. The yield of copolymer isolated was 78.7 g. This copolymer, which was 62.6 wt % ethylene, had a weight-average molecular weight of 105,000 and a molecular weight distribution of 4.94. Analysis by $^{13}$C NMR spectroscopy indicated a reactivity ratio ($r_1r_2$) of 0.153.

EXAMPLE 32

In this example, ethylene, propylene, and 1-butene were copolymerized in a hexane diluent by adding under a nitrogen atmosphere to a 1 L stainless-steel reactor, previously flushed with nitrogen and containing 400 ml of dry, oxygen-free hexane, 50 ml of a toluene solution containing 19 mg of bis(cyclopentadienyl)hafnium dimethyl and 15 mg of tri(n-butyl)ammonium tetra(pentafluorophenyl)boron. 1-butene (50 ml) and propylene (25 ml) were added to the autoclave, which was further pressurized with 60 psig of ethylene. The autoclave was stirred at 50C. for 45 minutes, then cooled and vented. The contents were dried under a stream of air. The yield of isolated terpolymer was 17.9 g. The weight-average molecular weight of the polymer was 188,000 and the molecular weight distribution was 1.89. Analysis by $^{13}$C NMR spectroscopy indicated that the polymer contained 62.9 mole % ethylene, 25.8 mole % propylene, and 11.3 mole % butene.

EXAMPLE 33

In this example, ethylene, propylene, and 1,4-hexadiene were copolymerized in a hexane diluent by adding under a nitrogen atmosphere to a 1 L stainless-steel autoclave, previously flushed with nitrogen and containing 400 ml of dry, oxygen-free hexane, first 100 ml of freshly-distilled 1,4-hexadiene, then 50 ml of a catalyst solution containing 72 mg of bis(cyclopentadienyl)hafnium dimethyl and 16 mg N,N-dimethylanilinium tetra(perfluorophenyl)boron. Propylene (50 ml) was added to the autoclave, which was further pressurized with 90 psig of ethylene. The autoclave was stirred at 50C. for 10 minutes, then cooled and vented. The contents were dried under a stream of air. The yield of isolated terpolymer was 30.7 g. The weight-average molecular weight of the polymer was 191,000 and the molecular weight distribution was 1.61. Analysis by $^{13}$C NMR spectroscopy indicated that the polymer contained 70.5 mole % ethylene, 24.8 mole % propylene, and 4.7 mole % 1,4-hexadiene.

EXAMPLE 34

In this example, ethylene and 1-hexene were copolymerized in a hexane diluent by adding under a nitrogen atmosphere to a 1 L stainless-steel autoclave, previously flushed with nitrogen and containing 400 ml of dry, oxygen-free hexane, first 30 ml of toluene solution containing 15 mg of bis(cyclopentadienyl)hafnium dimethyl, then, after 5 minutes, 100 ml of alumina-filtered and degassed 1-hexene and then 50 ml of a toluene solution containing 12 mg of bis(cyclopentadienyl)hafnium dimethyl and 30 mg of tri(n-butyl)ammonium tetra(pentafluorophenyl)boron. The autoclave was pressurized with 65 psig of ethylene, stirred and heated at 50C. for 1 hour, then cooled and vented. The contents were dried in a vacuum oven. The yield of isolated copolymer was 54.7 g. The copolymer, which was 46 wt % ethylene, had a weight-average molecular weight of 138,000 and a molecular weight distribution of 3.08. Analysis by $^{13}$C NMR spectroscopy indicated a reactivity ratio $(r_1r_2)$ Of 0.262.

EXAMPLE 35

In this example, propylene was polymerized in a hexane diluent by adding under a nitrogen atmosphere to a 1 L stainless-steel autoclave, previously flushed with nitrogen and containing 200 ml of dry, oxygen-free hexane, 50 ml of a toluene solution containing 72 mg of bis(cyclopentadienyl)hafnium dimethyl and 22 mg of N,N-dimethylanilinium tetraks(pentafluorophenyl)boron. Propylene (200 ml) was added and the autoclave was stirred at 40C. for 65 minutes. The autoclave was cooled and vented and the contents dried in a vacuum oven. The yield of atactic polypropylene was 37.7 g. The weight-average molecular weight of this polymer was 92,000 and the molecular weight distribution was 1.54.

EXAMPLE 36

In this experiment, propylene was polymerized in bulk propylene by adding under a nitrogen atmosphere to a 1 L stainless-steel autoclave, previously flushed with nitrogen, 50 ml of a toluene solution containing 77 mg of bis(cyclopentadienyl)hafnium dimethyl and 22 mg of N,N-dimethylanilinium tetra(pentafluorophenyl)boron. Propylene (400 ml) was added and the autoclave stirred at 40C. for 90 minutes. The autoclave was cooled and vented and the contents dried in a vacuum oven. The yield of atactic polypropylene isolated was 58.7 g. The weight-average molecular weight of this polymer was 191,000 and the molecular weight distribution was 1.60.

EXAMPLE 37

In this example, propylene was polymerized in bulk propylene by washing 72 mg of bis(cyclopentadienyl)hafnium dimethyl and 22 mg of N,N-dimethylanilinium tetra(pentafluorophenyl)boron into a 1 L stainless-steel autoclave, previously flushed with nitrogen, with 500 mL of propylene. The autoclave was stirred at 40C. for 90 minutes and at 50C. for another 30 minutes, then cooled and vented. 2.3 g of atactic polypropylene were isolated.

EXAMPLE 38

In this example, ethylene was polymerized by reacting 55 mg of bis(trimethylsilylcyclopentadienyl)hafnium dimethyl with 80 mg of N,N-dimethylanilinium tetra(pentafluorophenyl)boron in 5 ml of toluene in a serum-capped vial. On passing ethylene through the solution for 15 seconds, polymer formed as the mixture grew hot. The vial was opened and the contents diluted with acetone, filtered, washed, and dried. The yield of polyethylene was 0.26 g.

EXAMPLE 39

In this example, propylene was polymerized in bulk propylene by adding under a nitrogen atmosphere to a 1 L stainless-steel autoclave, previously flushed with nitrogen, 25 ml of a toluene solution containing 10 mg of rac-dimethylsilylbis(indenyl)hafnium dimethyl and 5 mg of N,N-dimethylanilinium tetrakis (pentafluorophenyl) boron. Propylene (500 ml) was added and the autoclave stirred at 40C. for 4.5 hours. The autoclave was cooled and vented and the contents dried in a vacuum oven. The yield of isotactic polypropylene isolated was 78.5 g. The weight-average molecular weight of this polymer was 555,000 and the molecular weight distribution was 1.86. The polymer had a melting point of 139C. Analysis by $^{13}$C NMR spectroscopy indicated that the polymer was about 95% isotactic.

EXAMPLE 40

In this example, an active ethylene polymerization catalyst was prepared by suspending 40 mg of N,N-dimethylanilinium tetrakis (pentafluorophenyl)boron and 17 mg of 1-bis(cyclopentadienyl)zircona-3-dimethylsilacyclobutane in 10 ml of toluene in a septum-capped round bottomed flask. Passage of ethylene through the solution for 30 seconds caused the solution to become hot as polymer precipitated. The flask was opened and the contents diluted with acetone. The polymer was filtered off, washed with acetone, and dried in vacuo. The yield of polymer isolated was 0.15 g.

EXAMPLE 41

In this example, an active ethylene polymerization catalyst was prepared by suspending 36 mg of 1-bis(cyclopentaienyl)titana-3-dimethyl-silacyclobutadiene and 80 mg of N,N-dimethylanilinium tetrakis(pentafluorophenyl)boron in 20 ml of toluene in a serum-capped round-bottomed flask. The solution darkened when ethylene was passed through it. After 5 minutes, the flask was opened and the contents diluted with ethanol. The polymer was filtered off, washed with ethanol, and dried. The yield of polyethylene isolated was 0.51 g.

EXAMPLE 42

In this example, an active ethylene polymerization catalyst was prepared by suspending 29 mg of (pentamethylcyclopentadienyl)(tetramethylethylene)cyclopentadienyl)zirconium phenyl and 43 mg of tri(n-butyl)ammonium tetrakis (pentafluorophenyl)boron in 25 ml of toluene in a serum-capped round bottomed flask. On passing ethylene through the solution, polymer formed almost instantly. After 5 minutes, the flask was opened and the contents diluted with ethanol. The polymer was filtered off, washed with acetone, and dried. The yield of polyethylene isolated was 0.49 g.

EXAMPLE 43

In this example, an active ethylene polymerization catalyst was prepared by suspending 34 mg of bis(cyclopentadienyl)zirconium (2,3-dimethyl-1,3-butadiene) and 85 mg of tri(n-butyl)ammonium tetra(pentafluorophenyl)boron in 50 ml of toluene in a serum-capped bottle. On introducing ethylene, the solution grew warm instantly as polymer precipitated. After 5 minutes the bottle was opened and the contents diluted with ethanol. The polymer formed was filtered off, washed with ethanol, and dried. The yield of polymer isolated was 1.06 g.

EXAMPLE 44

In this example, ethylene was polymerized by reacting 20 mg of 1-bis(cyclopentadienyl)hafna-3-dimethylsilacyclobutane and 39 mg of N,N-dimethylanilinium tetra(pentafluorophenyl)boron in 20 ml of toluene in a serum-capped round-bottomed flask. On passing ethylene through the solution, polymer precipitated as the solution grew warm. After 1 minute, the flask was opened and the contents diluted with ethanol. The polymer was filtered off, washed with ethanol, and dried. The yield of polyethylene isolated was 0.263 g.

EXAMPLE 45

In this example, ethylene was polymerized by reacting 21 mg of bis(cyclopentadienyl)hafnium (2,3-dimethyl-1,3-butadiene) and 41 mg of tri(n-butyl)ammonium tetra(pentafluorophenyl)boron in 50 ml of toluene in a serum capped bottle. On passing ethylene through the solution, polymer precipitated within seconds. After 10 minutes, the bottle was opened and the contents diluted with ethanol. The solid polymer was filtered off, washed with acetone, and dried. The yield of polyethylene isolated was 0.93 g.

EXAMPLE 46

In this example, ethylene was polymerized by reacting 53 mg of (pentamethylcyclopentadienyl)(tetramethylcyclopentadienylmethylene)hafnium benzyl and 75 mg of N,N-dimethylanilinium tetrakis(pentafluorophenyl)boron in 50 ml of toluene in a serum-capped bottle. Ethylene was passed through the solution for 10 minutes. The bottle was opened and the contents diluted with ethanol. The polymer was filtered off, washed with acetone, and dried. The yield of polyethylene isolated was 0.65 g.

While the present invention has been described and illustrated by reference to particular embodiments thereof, it will be appreciated by those of ordinary skill in the art that the same lends itself to variations not necessarily illustrated herein. For this reason, then, reference should be made solely to the appended claims for purposes of determining the true scope of the present invention.

We claim:

1. An ionic polymerization catalyst comprising (1) a cation derived from a bis(cyclopentadienyl) Group IV-B metal compound by abstracting a ligand to create a positively charged species and (2) a stabilizing non-coordinating anion, said anion being sufficiently labile to permit displacement by an olefin, diolefin and/or acetylenically unsaturated monomer during polymerization.

2. A composition of matter comprising a Group IV-B metal cation and a non-coordination anion, which composition is represented by one of the following general formulae:

  (1)

  (2)

wherein:

(A—Cp) is either (Cp)Cp') or Cp—A'—Cp'; Cp and Cp' are the same or different cyclopentadienyl rings substituted with from zero to five substituent groups S, each substituent group S being, independently, a radical group which is hydrocarbyl, substituted-hydrocarbyl, halocarbyl, substituted-halocarbyl, hydrocarbyl-substituted organometalloid, halocarbylosubstituted organometalloid or halogen radical, or Cp and Cp' are cyclopentadienyl rings in which any two adjacent S groups are joined forming a $C_4$ to $C_{20}$ ring to give a saturated or unsaturated polycyclic cyclopentadienyl ligand; and A' is a bridging group restricting rotation of the Cp and Cp' rings;

M is titanium, zirconium or hafnium;

L' is a neutral Lewis base;

$X_1$ is a hydride radical, hydrocarbyl radicals, substituted-hydrocarbyl radicals, hydrocarbyl-substituted organometalloid radicals or halocarbyl-substituted organometalloid radical;

$X_5$ is a hydride radical, hydrocarbyl radical or substituted-hydrocarbyl radical or substituted organometalloid radicals, which radical may optionally be covalently bonded to both M and L';

B' is a compatible non-coordinating anionic complex; and d is an integer representing the charge of B'.

3. The composition of claim 2, wherein B' is a single anionic complex comprising a plurality of lipophilic radicals covalently bonded to and shielding a central charge-bearing metal or metalloid atom, or a plurality of boron atoms.

4. The composition of claim 3 wherein B' is represented by the general formula:

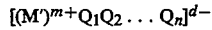

wherein:

M' is a metal or metalloid;

$Q_1$ to $Q_n$ are, independently, hydride radicals, bridged or unbridged dialkylamido radicals, alkoxide and aryloxide radicals, substituted-hydrocarbyl radicals, halocarbyl and substituted-halocarbyl radicals, and hydrocarbyl- and halocarbyl-substituted organometalloid radicals and any one, but not more than one, of Q1 to Qn may be a halide radical.

5. The composition of matter according to claim 2 wherein the substitutent group S on any of Cp, Cp', $X_1$, or $X_5$ is independently a $C_1$ to $C_{20}$ radical.

6. The composition of claim 4, wherein at least one of $Q_1$ to $Q_n$ is pentafluorophenyl.

7. The composition of claim 4, wherein B' is represented by the formula:

$$[BAr_1Ar_2X_3X_4]-$$

wherein:

B is boron in a valence state of 3+;

$Ar_1Ar_2$ are the same or different aromatic or substituted-aromatic hydrocarbon radicals and may be linked to each other through a stable bridging group; and $X_3X_4$ are, independently, hydride radicals, halide radicals, with the proviso that only one of $X_3$ or $X_4$ will be halide, hydrocarbyl radicals, substituted-hydrocarbyl radicals, halocarbyl radicals, substituted-halocarbyl radicals, hydrocarbyl- and dialkylamido radicals, and alkoxide and aryloxide radicals.

8. The composition of claim 2, which composition has the following general formula:

$$\{[(A-Cp)MX_1]_d[B']\}^{3-}.$$

9. The composition of claim 3, wherein B' is a non-coordinating aryl boron anion.

10. The composition of claim 9, wherein the aryl boron anion is $[B(C_6F_5)_4]-$ or $[B(C_6F_5)_3Q]-$ where Q is a monoanionic, non-bridging hydride, hydrocarbyl, substituted-hydrocarbyl-substituted organometalloid, halocarbyl-substituted organometalloid, dialkylamido, alkoxy, aryloxy, or halide radical.

11. The composition of claim 10, wherein the aryl boron anion is $[B(C_6F_5)_4]-$.

12. The composition of claim 5, wherein (A—Cp) is (Cp)(Cp') and Cp and Cp' are the same or different substituted or unsubstituted cyclopentadienyl radicals wherein the substituted cyclopentadienyl radicals are substituted with from 1 to 5 substituent groups S.

13. The composition of claim 12, wherein (A—Cp) is $(C_5(CH_3)_5)_2$ or $(C_5H_5)_2$, M is Zr or Hf, and $X_1$ is methyl.

14. The composition of claim 12, wherein (A—Cp) is Cp—A'—Cp' and Cp—A'—Cp, forms a chiral ligand set.

15. The composition of claim 8, wherein (A—Cp) is Cp—A'—Cp' wherein Cp and Cp' are independently, substituted cyclopentadienyl radicals such that Cp and Cp' have different steric characteristics, or Cp is an unsubstituted cyclopentadienyl radical and Cp' is a substituted cyclopentadienyl radical.

* * * * *

UNITED STATES PATENT AND TRADEMARK OFFICE
CERTIFICATE OF CORRECTION

PATENT NO.    : 5,384,299
DATED         : January 24, 1995
INVENTOR(S)   : Howard W. Turner, et al It is certified that error appears in the above-indentified patent and that said Letters Patent is hereby corrected as shown below:

Column 38, lines 53 to 54, in Claim 3, delete the phrase ", or a plurality of boron atoms".

Signed and Sealed this

Nineteenth Day of September, 1995

Attest:

BRUCE LEHMAN

*Attesting Officer*     *Commissioner of Patents and Trademarks*